(12) United States Patent
Turbett et al.

(10) Patent No.: US 10,391,435 B2
(45) Date of Patent: Aug. 27, 2019

(54) STERILIZING METHOD AND APPARATUS

(71) Applicant: Turbett Surgical LLC, Rochester, NY (US)

(72) Inventors: Robert E. Turbett, Penfield, NY (US); Brian E. McGrath, Clarence, NY (US); Richard D. Richmond, Canandaigua, NY (US)

(73) Assignee: Turbett Surgical LLC, Rochester, NY (US)

( * ) Notice: Subject to any disclaimer, the term of this patent is extended or adjusted under 35 U.S.C. 154(b) by 0 days.

(21) Appl. No.: 15/946,442

(22) Filed: Apr. 5, 2018

(65) Prior Publication Data

US 2018/0221803 A1 Aug. 9, 2018

Related U.S. Application Data

(63) Continuation-in-part of application No. 15/461,895, filed on Mar. 17, 2017, now Pat. No. 10,226,728, which is a continuation of application No. 14/584,751, filed on Dec. 29, 2014, now Pat. No. 9,616,368, which is a continuation-in-part of application No. 14/167,691, filed on Jan. 29, 2014, now Pat. No. 10,245,335.

(60) Provisional application No. 62/482,170, filed on Apr. 5, 2017, provisional application No. 62/482,683, filed on Apr. 6, 2017, provisional application No. 62/483,008, filed on Apr. 7, 2017.

(51) Int. Cl.
*A61L 2/07* (2006.01)
*B01D 25/02* (2006.01)
*B01D 29/54* (2006.01)
*B01D 46/00* (2006.01)
*A61L 2/26* (2006.01)
*B01D 46/10* (2006.01)

(52) U.S. Cl.
CPC ............ *B01D 46/0005* (2013.01); *A61L 2/26* (2013.01); *B01D 46/0002* (2013.01); *B01D 46/0023* (2013.01); *A61L 2/07* (2013.01); *A61L 2202/121* (2013.01); *A61L 2202/15* (2013.01); *A61L 2202/182* (2013.01); *A61L 2202/23* (2013.01); *A61L 2202/24* (2013.01); *B01D 46/0024* (2013.01); *B01D 46/10* (2013.01); *Y10T 29/49826* (2015.01)

(58) Field of Classification Search
CPC ....... A61L 2/07; A61L 2202/24; B01D 25/02; B01D 29/54; B01D 46/0002; B01D 46/0023
USPC ............ 422/26, 292, 295, 298, 300; 55/315; 96/108, 136
See application file for complete search history.

(56) References Cited

U.S. PATENT DOCUMENTS

| | | | |
|---|---|---|---|
| 3,925,043 A | 12/1975 | Matrone et al. | |
| 5,369,892 A | 12/1994 | Dhaemers | |
| 5,968,459 A * | 10/1999 | Nalepa | A61L 2/07 206/439 |

* cited by examiner

*Primary Examiner* — Monzer R Chorbaji
(74) *Attorney, Agent, or Firm* — Brian B. Shaw, Esq.; Jodi A. Reynolds, Esq.; Harter Secrest & Emery LLP

(57) ABSTRACT

A sterilization container for retaining surgical instruments in a sterilizer comprising a plurality of walls defining an interior volume sized to receive at least one instrument tray, least one of the walls defining a venting pass through area, and a filter occluding the venting passage area, wherein a ratio of the venting pass through area to the interior volume is at least 1 square inch:125 cubic inches.

19 Claims, 31 Drawing Sheets

STERILIZING METHOD AND APPARATUS

BACKGROUND OF THE INVENTION

Field of the Invention

Exemplary embodiments of the present disclosure relate to a method and apparatus for sterilization and more particularly to a method and apparatus for sterilization of instruments, wherein a ratio of venting pass through area to volume of the sterilization container is at least a given value, and wherein the given value in select configurations can provide a drying time of less than 30 minutes and in select configurations less than 15 minutes.

Description of Related Art

Sterilization is a term referring to any process that eliminates (removes) or kills microbial life, including transmissible agents (such as fungi, bacteria, viruses, or spore forms) present on a surface, or contained in a fluid, or in medication, or in a compound such as biological culture media. Sterilization can be achieved by applying heat, chemicals, irradiation, high pressure, and filtration or combinations thereof.

In general, surgical instruments and medications that enter an already aseptic part of the body (such as the bloodstream, or penetrating the skin) must be sterilized to a high sterility assurance level. Examples of such instruments include scalpels, hypodermic needles and implantable medical devices (IMD), such as artificial pacemakers.

A widely used method for heat sterilization is the autoclave, sometimes referred to as a sterilizer. Autoclaves commonly use steam heated to 121-134° C. To achieve a degree of sterility, a holding time of at least 15 minutes at 121° C. at 100 kPA, or 3 minutes at 134° C. at 100 kPa is required. Additional sterilizing time is usually required for liquids and instruments packed in layers of cloth, as they may take longer to reach the required temperature.

One method of sterilization involves passing steam through a container. For effective sterilization, steam needs to penetrate the container load uniformly. Accordingly, the container must not be overcrowded, and the lids of bottles and containers must be left ajar. During the initial heating of the container, residual air must be removed. Indicators should be placed in the most difficult places for the steam to reach to ensure that steam actually penetrates there.

A filter is typically placed over the vent to keep particles or extraneous materials from entering the container before, during or after the sterilizing process. Once the sterilizing process is completed, the filter needs to be removed and inspected by medical professionals to verify the integrity of the sterilizing process was maintained. If it is discovered during inspection that the filter did not remain intact, the sterilizing process has to be repeated with a new filter. Further, if moisture is present in the container, the load would be rejected by the user and sent for reprocessing. Thus, a sufficient drying time, wherein there is no visible moisture on the sterilized medical instruments, is needed before the sterilization processing is complete.

The amount of drying time needed to achieve a dry load can be significant. Dry time can add several minutes to the total processing time in order to achieve a load where the instruments are dry. Further, heavier loads, for example, those with a large metal mass, can cause moisture to be maintained inside the container after the sterilization cycle is complete. Thus, weight limits may be required to avoid wet, unsterilized loads after processing. In existing devices, a sterilization cycle may run for 4 minutes at 270° F., followed by at least a 30 minute dry cycle. These containers have relatively small vent area to volume ratios, wherein an area of the vent is small compared to the internal volume of the container. For example, in the S.C.O.R.E.S. container labelled by PMBS, LLC of Stockton N.J., the ratio of the area of the vent to volume is approximately 0.004-0.006 $in^2$ per $in^3$. These vent area to volume ratios limit circulation through the container, contribute to the longer dry times required for achieving a dry load, and significantly limit the weight of the load that can be placed into the container.

What is needed, then, is a sterilization container for retaining surgical instruments in a sterilizer that has improved circulation and evaporation and shorter drying times.

BRIEF SUMMARY OF THE INVENTION

In view of the foregoing, a sterilization container for retaining a surgical instrument in a sterilizer is provided.

A first exemplary embodiment provides a sterilization container for retaining surgical instruments in a sterilizer. The sterilization container comprises an enclosing wall and a door defining an interior volume sized to receive at least one instrument tray, at least one of the enclosing wall and the door defining a venting pass through area, and a filter occluding the venting pass through area, wherein a ratio of the venting pass through area to the interior volume is at least 0.008 $inch^2$ per $inch^3$, and in select configurations at least 0.016 $inch^2$ per $inch^3$, and in further configurations greater than 0.02 $inch^2$ per $inch^3$. In further configurations, the ratio of the venting pass through area to the interior volume is between least 0.008 $inch^2$ per $inch^3$ and 0.2 $inch^2$ per $inch^3$ and in select configurations between 0.016 $inch^2$ per $inch^3$, and 0.2 $inch^2$ per $inch^3$.

The enclosing wall of the sterilization container can be any of a variety of configurations, such as but not limited to defining polygonal containers, containers with curvilinear walls or combinations thereof. For purposes of description, the sterilization container has been set for in terms of walls forming the enclosing wall. Thus, in a further configuration, the sterilization container comprises an enclosing wall having a plurality of walls and a door defining an interior volume sized to receive at least one instrument tray, at least one of the walls and the door defining a venting pass through area, and a filter occluding the venting passage area, wherein a ratio of the venting pass through area to the interior volume is at least 0.008 $inch^2$ per $inch^3$, and in select configurations at least 0.16 $inch^2$ per $inch^3$, and in further configurations greater than 0.2 $inch^2$ per $inch^3$.

Further, the configurations are set forth in terms of a sterilization container, which encompasses a sterilization cabinet.

Another exemplary embodiment provides a method of drying contents in a sterilization container, the method comprising sterilizing contents in a sterilization container having an enclosing wall, such as a plurality of walls, and a door defining an interior volume sized to receive at least one instrument tray retaining the contents, venting the sterilization container through a venting pass through area having a filter occluding the venting passage area, wherein a ratio of the venting pass through area to the interior volume is at least 0.008 $inch^2$ per $inch^3$, and obtaining a drying of the contents in the sterilizing cabinet in less than 30 minutes and in select configurations less than 15 minutes.

A further exemplary embodiment provides a sterilization container for retaining surgical instruments in a sterilizer, the sterilization container comprising an enclosing wall, such as a plurality of walls and a door defining an interior volume sized to receive at least one instrument tray, at least one of the enclosing wall and the door defining a venting pass through area, and a filter occluding the venting passage area, the sterilization container having a ratio of the venting pass through area to the interior volume sufficient to provide a drying time of less than 30 minutes and in select configurations less than 15 minutes.

BRIEF DESCRIPTION OF THE SEVERAL VIEWS OF THE DRAWING(S)

DETAILED DESCRIPTION OF THE INVENTION

Figure 1A:
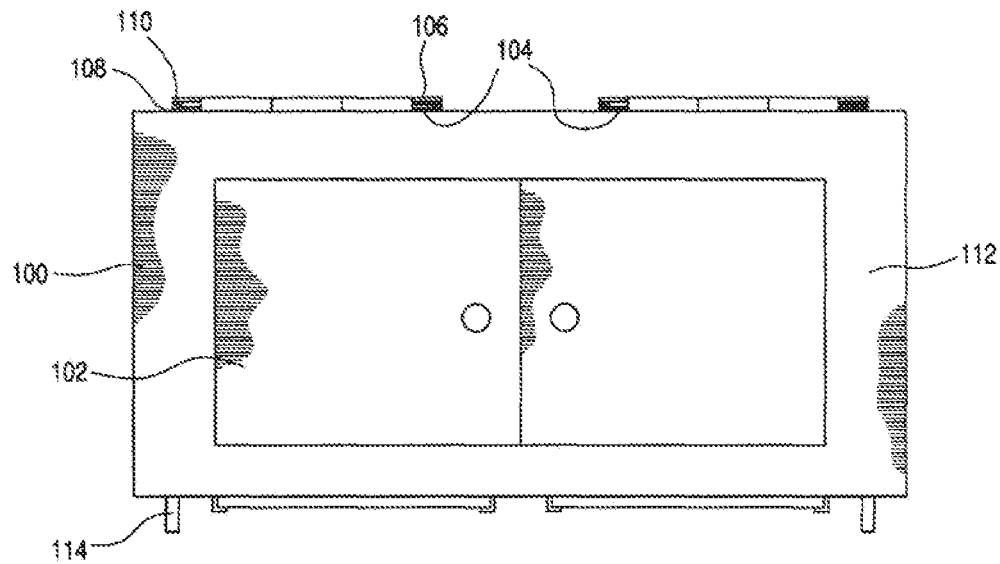
FIG. 1a is a front view of a configuration of a sterilization container such as a sterilization cabinet suitable for use in practicing exemplary embodiments of this disclosure.

In the medical field, it is of the utmost importance that medical instruments are sterilized prior to any medical procedure. This drastically helps prevent the spread of infectious materials. In the marketplace, there are a wide variety of devices that provide for sterilization of medical instruments through the use of a sterilizing agent, such as steam. Instrument trays can be wrapped in a cloth or paper that acts as a filter, allowing the tray to be sterilized, then delivered to the operating room. Alternatively, a rigid container can contain the instrument tray. The device (e.g., a rigid container, sterilization container or cabinet) contains at least one vent for venting the steam used to sterilize the contents of the device. A disposable filter usually covers these vents. The filters have two major purposes. First, the filters prevent extraneous materials from entering the sterilizing device during and after the sterilization cycle. Second, the filters allow sterilizing steam to enter and exit the sterilizing device (sterilization container). Thus, the sterilization container can retain the sterilized medical instruments within the container and protected from the environment by the filters sealing the vents. The filter can be made of any type of porous paper or cellulose type material. In other embodiments, the filter is made of polymeric substances, such as polypropylene or a combination such as plasticized paper as known in the art. The filter is required to be both porous and dense enough to allow the passage of a sterilizing agent, such as steam, through its membrane, but also resilient enough to not rip or tear during a sterilizing cycle or during insertion/clamping into operable position. Although the present description is set forth in terms of a paper-like filter, the filter can be a tortuous path or even a valve that acts as a check valve permitting the venting of the sterilization container without permitting passage of extraneous materials into the sterilization container.

Referring to FIGS. 1a-3b, the sterilization container 100, alternatively referred to as the sterilization cabinet is shown. For purposes of the present description, the sterilization container is set forth as a sterilization cabinet. However, it is understood, the disclosure is not limited to the sterilization cabinet and can be any sterilization container. And further, it should be noted that embodiments of the present invention are not limited to the particular configuration of sterilizing cabinet 100.

The term sterilization cabinet 100 encompasses any device capable of retaining the medical instruments subjected to the sterilization procedure, wherein the cabinet 100 can receive and retain at least one tray, with the tray retaining at least one medical instrument. The sterilization cabinet 100 can retain the medical instruments in the sterilized condition after the sterilization process. The term sterilization container also includes sterilizing cabinets for sterilizing medical instruments, surgical devices and the like. The term sterilizer includes, but is not limited to, a housing or device defining an interior retaining the sterilization container and in which a controlled environment is create to impart a desired sterilization. Sterilizers include autoclaves; hot air ovens; ethylene oxide; low temperature steam, steam, high pressure steam and formaldehyde; sporicidal chemicals; irradiation; chlorine dioxide (CD) gas sterilization; hydrogen peroxide; vaporized hydrogen peroxide; hydrogen peroxide plasma; electron beam and gas plasma devices.

The sterilization cabinet 100 includes an enclosing wall which defines an interior volume, wherein the enclosing wall can include a plurality of sidewalls, a top wall and a bottom wall. The walls can be planar or curvilinear and can be oriented to define a rectilinear volume, cubic volume or round or curved volume. For purposes of the present disclosure, the enclosing wall is set forth as the plurality of sidewalls, the top wall and the bottom wall, along with a door. It is understood the enclosing wall can include or cooperate with a door to at least partially define the interior volume. In one configuration the sterilization cabinet 100 includes the enclosing wall having the plurality of sidewalls, the top wall and the bottom wall, along with a door or doors 102, vents 104, and in certain configurations filter holder 106, primary filter 108, secondary filter 110, sterilization cabinet frame 112 and legs 114. Door or doors 102 are able to open and close for access to the interior of sterilizing cabinet 100. Door or doors 102 are physically connected to sterilization cabinet frame 112. Door or doors 102 can be attached through the use of a hinge or hinges which allows the doors to swing open. Alternatively, door or doors 102 can be removable from sterilization cabinet 100 through the use of clamps (not shown in FIG. 1). It should be appreciated that exemplary embodiments of door or doors 102 include any mechanism that allows for door or doors 102 to move from an open position to a closed position to provide access to the interior of sterilization cabinet 100. The door can effectively form a wall of the sterilization cabinet, as seen in the Figures.

Sterilization cabinet 100 in one embodiment provides for four vents 104. However, it should be appreciated that exemplary embodiments of sterilizing cabinet 100 are not limited to four vents. The sterilization cabinet 100 may include a fewer number or a greater number of vents 104. The vents 104 can define a venting pass through area 140 of the sterilizing cabinet 100. It should be appreciated that vents 104 can provide numerous small openings for the passage of sterilizing steam or heat. The small openings in vents 104 can be holes or slits. Alternatively, vents 104 can be fenestrated. By "venting pass through area" it is meant to refer to the total available area for the ingress and egress of a gas to or from the interior volume of the sterilizing cabinet 100. Exemplary embodiments of sterilization cabinet 100 can include one or more vents so long as the venting pass through area to volume ratio is equal to or greater than 0.008 inch$^2$ per inch$^3$, or 1 inch$^2$:125 inch$^3$, and in select configurations between 0.02-0.2 inch$^2$ per inch$^3$, or between 1 inch:50 inch$^3$ and 1 inch$^2$:5 inch$^3$, and in further configurations between 0.16-0.2 inch$^2$ per inch$^3$, or 4 inch:25 inch$^3$ and 1 inch:5 inch$^3$.

The term "dry time" or "drying time" means the time required to provide no visible moisture in the sterilization container or on the sterilized medical instrument (or tray or wrapping, if used), as set forth in the governing regulations. For example, as set forth in AAMI ST79 Comprehensive guide to steam sterilization and sterility assurance in health care facilities (AAMI/CDV-2 ST79), visible moisture left in (interior) or on (exterior) a package or tray within the sterilization container after sterilization and the proper cooling (drying) period should be considered a wet pack. Further, if moisture is present on or in two or more packages the load should be considered a wet load. The moisture may be in the form of visible dampness, droplets, or puddles of water on or within a pack (or instrument or tray). If wet packs are observed in the processing area they should not be released. If wet packs are observed in the user area (e.g., in the OR) they should not be used.

Figure 1B:
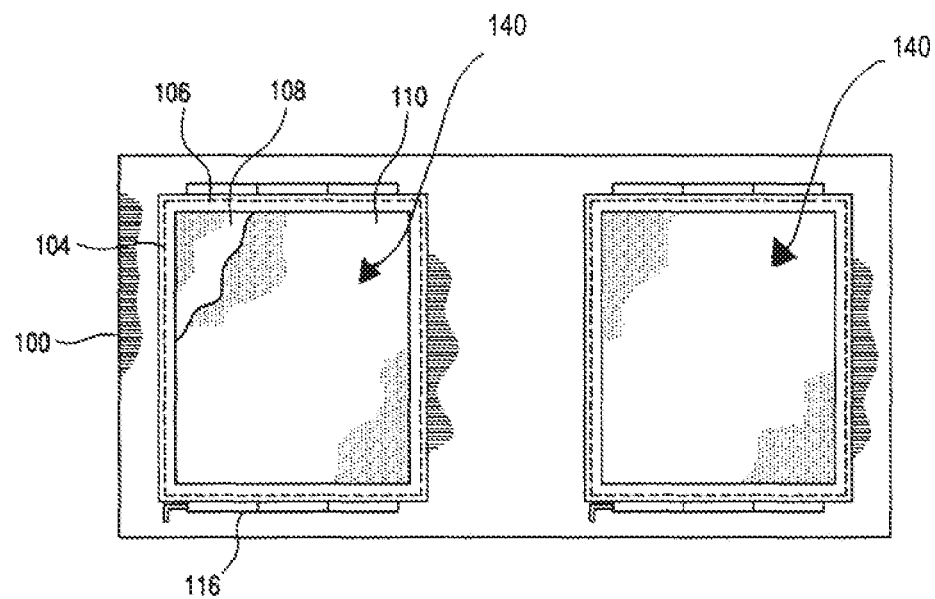
FIG. 1b is a top view of a configuration of a sterilization container such as a sterilization cabinet suitable for use in practicing exemplary embodiments of this disclosure.
Figure 1C:
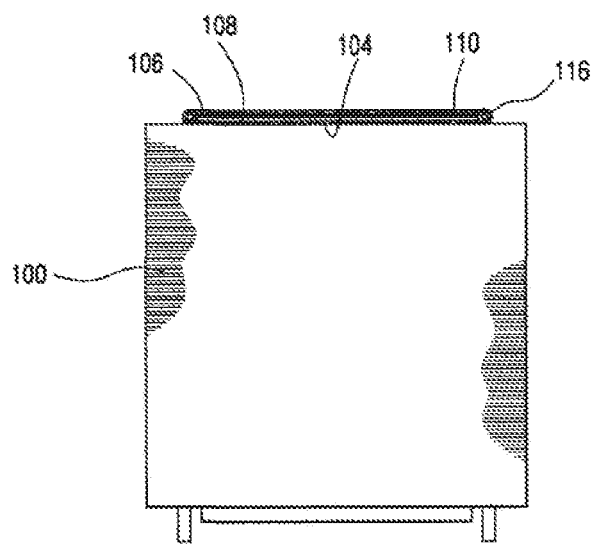
FIG. 1c is a side view of a configuration of a sterilization container such as a sterilization cabinet suitable for use in practicing exemplary embodiments of this disclosure.
Figure 2A:
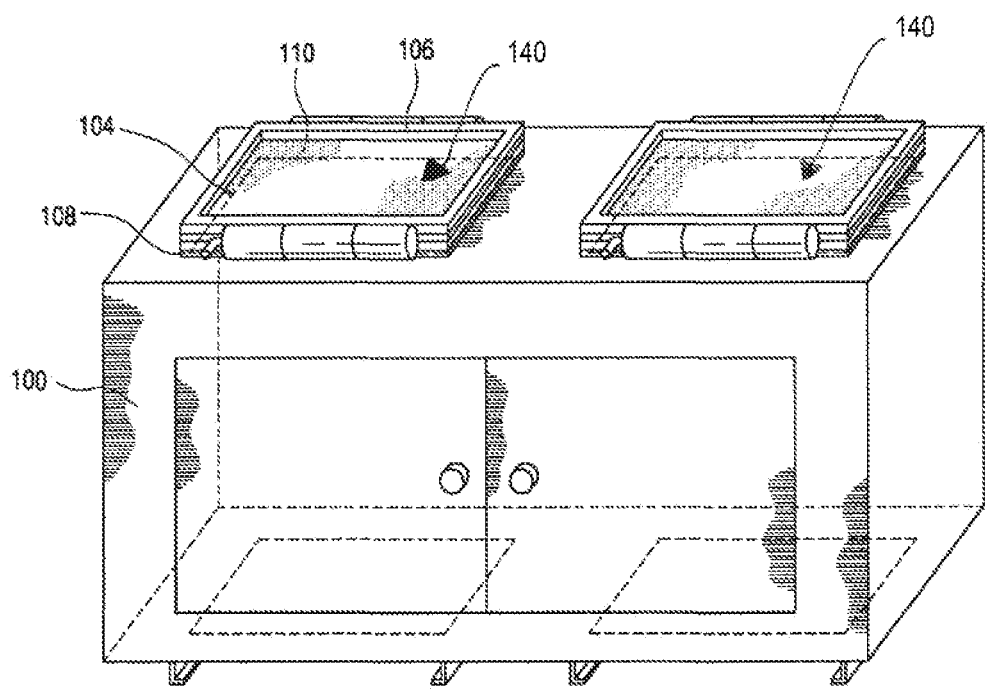
FIG. 2a is a perspective view of an alternative configuration of a sterilization container such as a sterilization cabinet suitable for use in practicing exemplary embodiments of this disclosure.
Figure 2B:
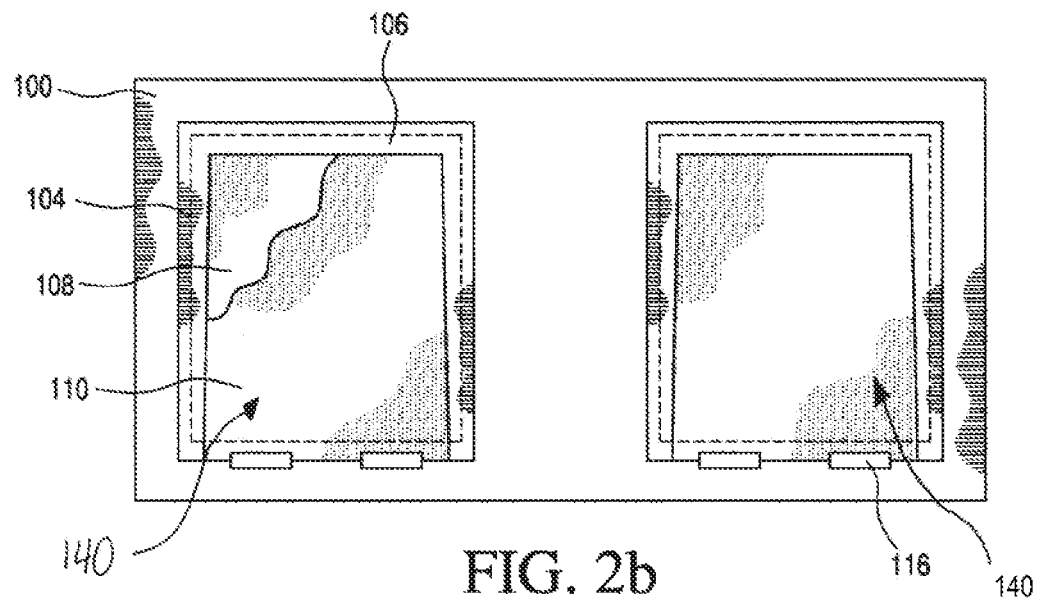
FIG. 2b is a top view of an alternative configuration of a sterilization container such as a sterilization cabinet suitable for use in practicing exemplary embodiments of this disclosure.
Figure 3A:
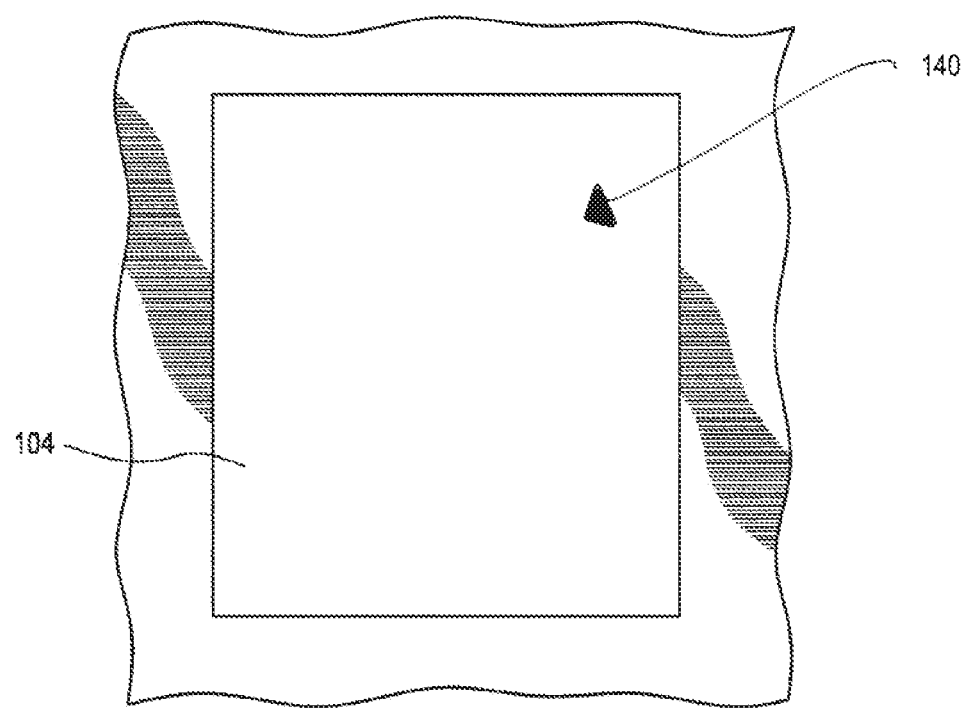
FIG. 3a is a top view of a vent of a sterilization container such as a sterilization cabinet suitable for use in practicing exemplary embodiments of this disclosure.
Figure 3B:
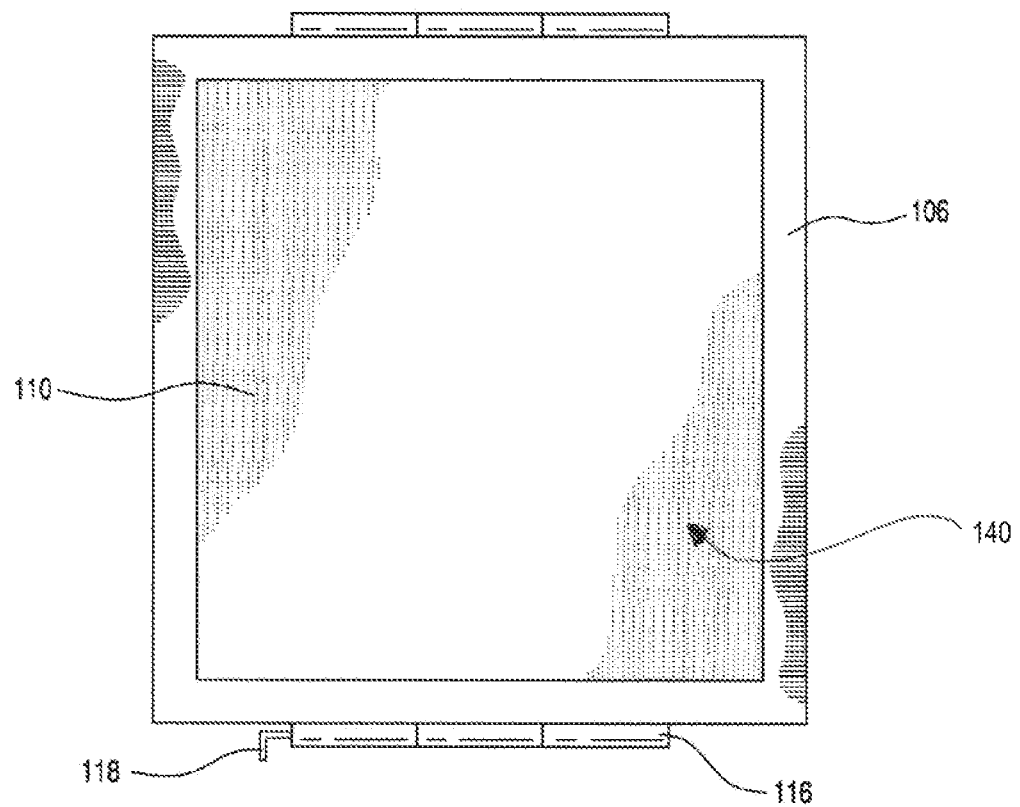
FIG. 3b is a perspective view of a filter arrangement of a sterilization container such as a sterilization cabinet for use in practicing exemplary embodiments of this disclosure.
Figure 4A:
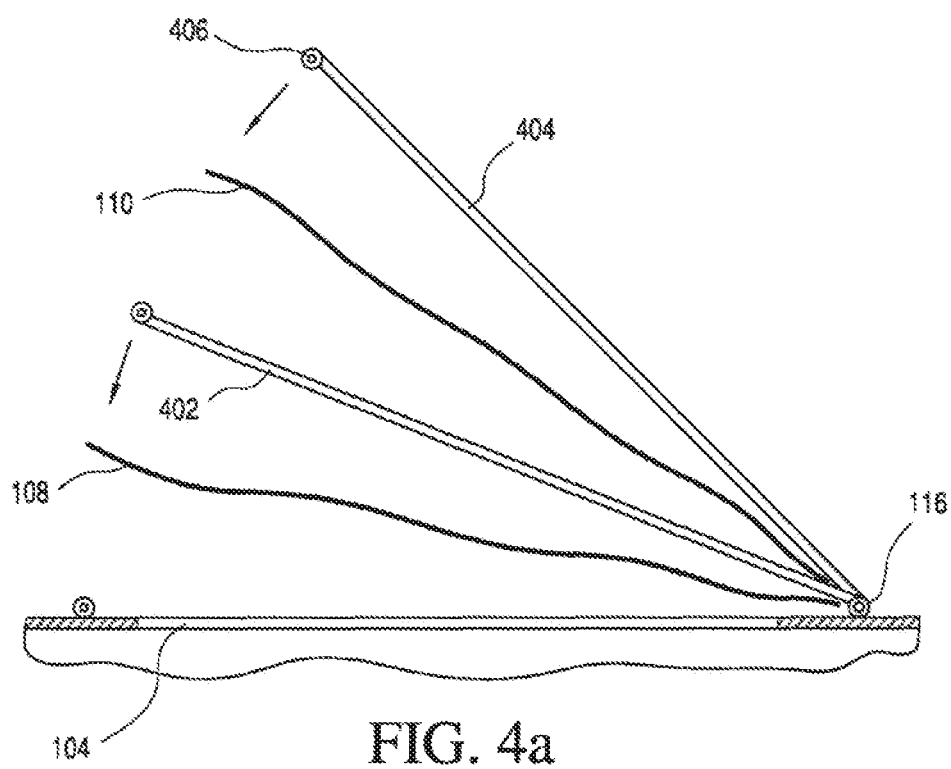
FIG. 4a is a perspective view of the movement of a filter arrangement of a sterilization container such as a sterilization cabinet for use in practicing exemplary embodiments of this disclosure.
Figure 4B:
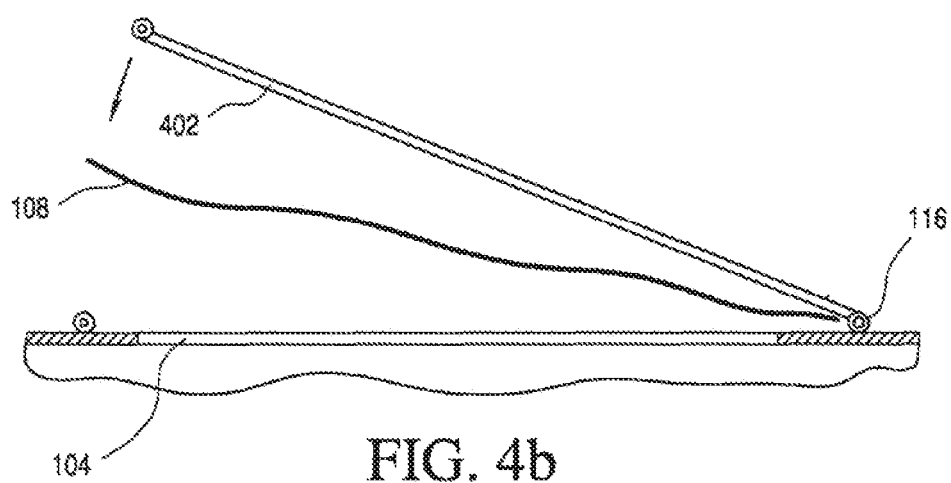
FIG. 4b is a perspective view of the movement of an alternative filter arrangement of a sterilization container such as a sterilization cabinet for use in practicing exemplary embodiments of this disclosure.

By "venting pass through area to volume ratio," it is meant the ratio of the total venting pass through area 140 of a sterilizing cabinet 100 to the interior volume of the sterilization cabinet 100 ratio. Thus, for example, a sterilizing cabinet 100 as shown in FIGS. 1a and 1b, with four vents 104, two vents 104 on the top of the sterilizing cabinet 100 and two vents 104 on the bottom of the sterilizing cabinet 100, each venting area having a venting area of approximately 11.4 inches ($L_2$)×13 inches ($W_2$), will have a total venting area of approximately 592 square inches. The volume of the sterilization cabinet 100, wherein the length is approximately 34 inches ($L_1$), the width is approximately 17 inches ($W_1$), and the height is approximately 17 inches ($H_1$), is approximately 9826 inches$^3$. Thus, sterilization cabinet 100 as shown in FIGS. 1a-2b would have a venting pass through area to volume ratio of approximately 0.06 inch$^2$ per inch$^3$. In other exemplary embodiments of the sterilization cabinet 100, the venting pass through area to volume ratio is between approximately 0.02-0.2 inch$^2$ per inch$^3$, or 1 square inch:50 cubic inches and 1 square inch:5 cubic inches, and in some configurations between 0.16-0.2 inch$^2$ per inch$^3$, or 4 square inches:25 cubic inches and 1 square inch:5 cubic inches. The high venting pass through area to volume ratio increases circulation and evaporation and reduces the drying time required after the sterilization cycle. It should be appreciated that exemplary embodiments of the sterilizing cabinet can be other dimensions, shapes and sizes that provide similar vent to volume ratios. For example, the upper limit of the venting pass through area to volume ratio is 6 inch$^2$ to 1 inch$^3$. However, from manufacturing considerations and structural requirements, the upper range of the venting pass through area to volume ratio is typically between 2.5 inch$^2$ and 6 inch$^2$ to 1 inch$^3$.

The sterilization cabinet 100 can retain multiple trays holding medical instruments and, because of the high venting pass through area to volume ratio, has a drying time of less than 30 minutes, and more specifically, between 10-15 minutes, and even more specifically 10 minutes. In one configuration, the sterilizing cabinet 100 can hold up to 15 trays and each tray holds up to 25 lbs of material to be sterilized. In a configuration of the invention, the dry time of less than 30 minutes includes multiple trays loaded into the sterilization cabinet 100, the trays holding a total of 140 lbs or less of material to be sterilized, and in select configurations less than 15 minutes dry time.

Figure 5A:
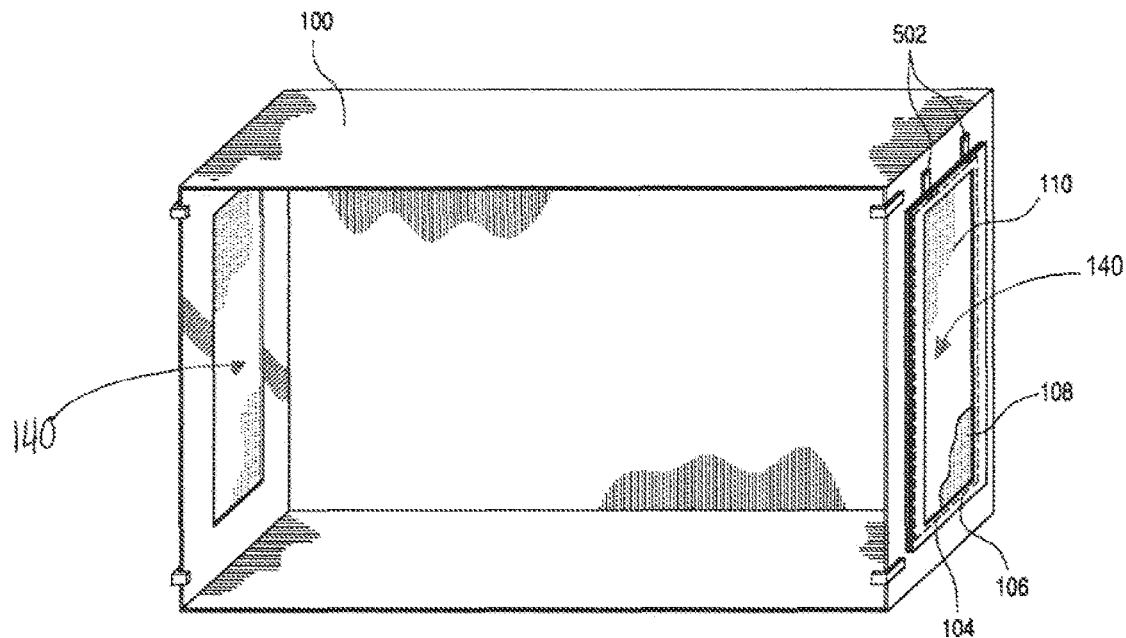
FIG. 5a is a perspective view of an alternative configuration of a sterilization container such as a sterilization cabinet suitable for use in practicing exemplary embodiments of this disclosure.
Figure 5B:
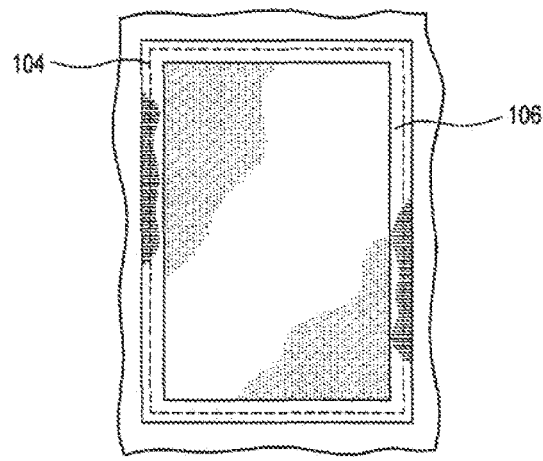
FIG. 5b is a perspective view of bottom section of a filter arrangement of a sterilization container such as a sterilization cabinet suitable for use in practicing exemplary embodiments of this disclosure.
Figure 5C:
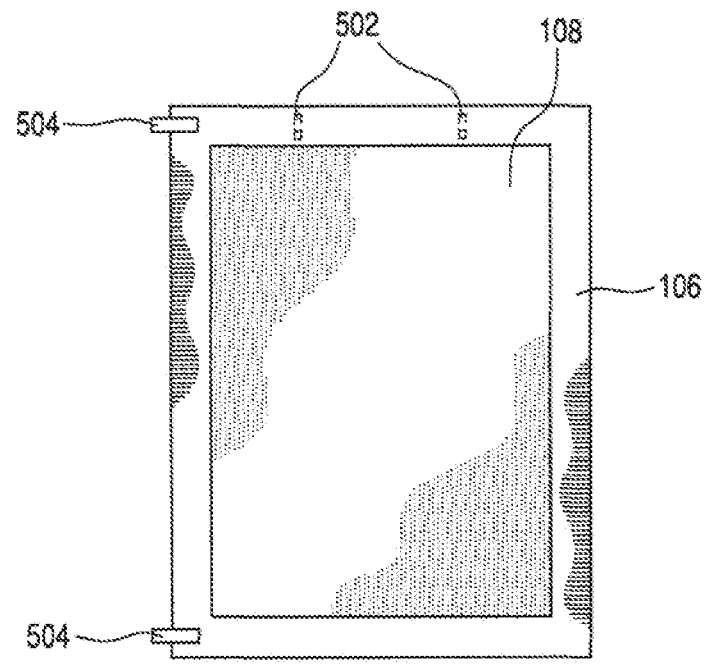
FIG. 5c is a perspective view of a middle section of a filter arrangement of a sterilization container such as a sterilization cabinet suitable for use in practicing exemplary embodiments of this disclosure.
Figure 5D:
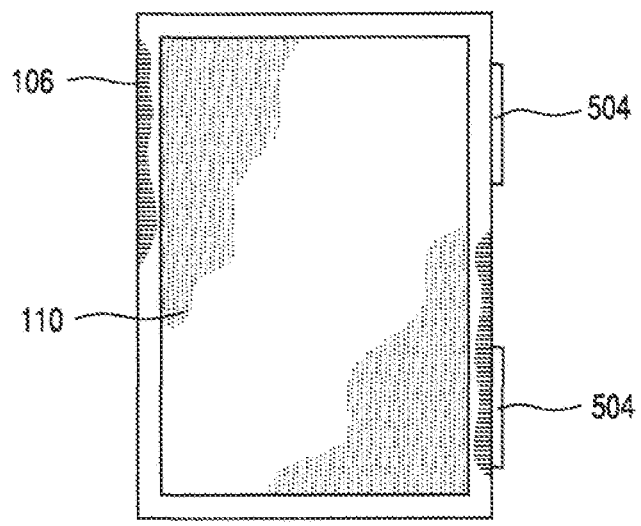
FIG. 5d is a perspective view of top section of a filter arrangement of a sterilization container such as a sterilization cabinet suitable for use in practicing exemplary embodiments of this disclosure.

FIG. 5a provides a perspective view of an alternative arrangement of sterilization cabinet 100 with vents 104 on the sides of the cabinet. In this embodiment filter holders 110 are located on the sides of sterilization cabinet 100 with primary filter 108 and secondary filter 110. Also shown in FIG. 5a are hangers 502 from which filter holder 106, primary filter 108 and secondary filter 110 attach to sterilizing cabinet 100. It can be appreciated that exemplary embodiments of sterilization cabinet 100 include vents 104, primary filter 108, secondary filter 110 and filter holder 106 on the side of sterilization cabinet 100. As shown in FIG. 5a, the vents 104 define a venting pass through area 140 of the sterilization cabinet 100. The sterilization cabinet 100 as shown in FIG. 5a having a vent 104 on each side of the sterilization cabinet 100. For the 34 inch by 22 inch by 24 inch sterilization cabinet 100, the venting area at each end as shown in the FIG is 20 inch by 22 inch providing a venting area of 440 inch$^2$ and the total venting area is approximately 880 inch$^2$ as there are two vents 104 having the same size in the configuration of the sterilization cabinet shown in FIG. 5a. The volume of the sterilization cabinet 100, wherein the length is approximately 34 inches, the width is approximately 20, and the height is approximately 24 inches, is approximately 17,952 inch$^3$. Thus, the sterilization cabinet 100 as shown in FIG. 5a would have a venting pass through area to volume ratio of approximately 0.049 inch$^2$ per inch$^3$, wherein the venting pass through area is approximately 880 inch$^2$ compared to the volume, which is 17,952 inch$^3$. In another configuration, the sterilization cabinet 100 includes 4 similarly dimensioned vents for the cabinet of 24 inches by 22 inches by 21 inches, providing a venting pass through area of approximately 1760 inch$^2$ compared a volume of approximately 11,000 inch$^3$ providing a venting pass through area to volume ratio of approximately 0.16 inch$^2$ per inch$^3$, or 4 square inches:25 cubic inches.

These high venting pass through area to volume ratios reduce the drying time required after the sterilization cycle. The sterilization cabinet 100 can hold multiple trays holding instruments and, because of the high venting pass through area to volume ratio, have a drying time of less than 30 minutes, and more specifically, between 10-15 minutes, and even more specifically 10 minutes. These trays can each hold up to 25 lbs of material to be sterilized. In a configuration of the invention, the dry time of less than 30 minutes includes multiple trays loaded into the sterilization cabinet 100, the trays holding a total of 140 lbs or less.

Figure 6A:
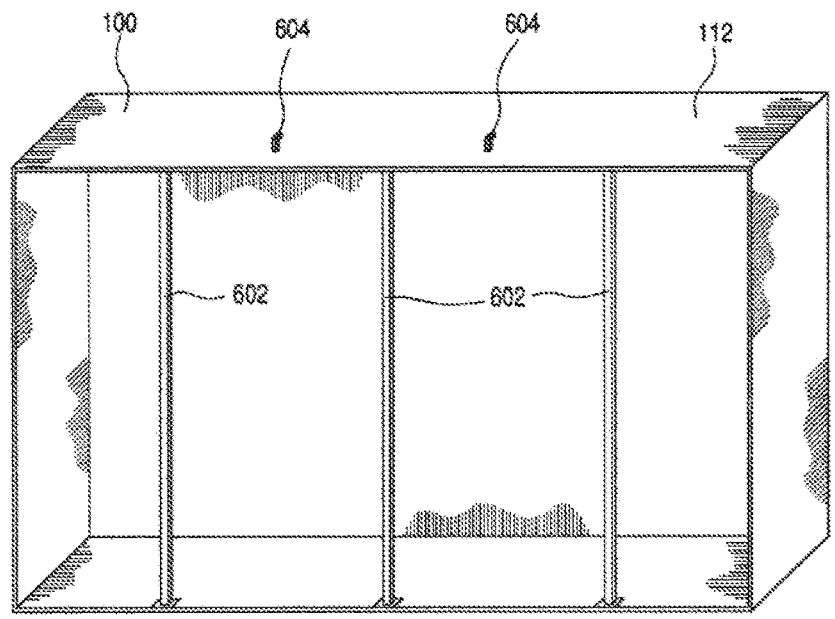
FIG. 6a is a perspective view of an alternative sterilization container such as a sterilization cabinet suitable for use in practicing exemplary embodiments of this disclosure.
Figure 6B:
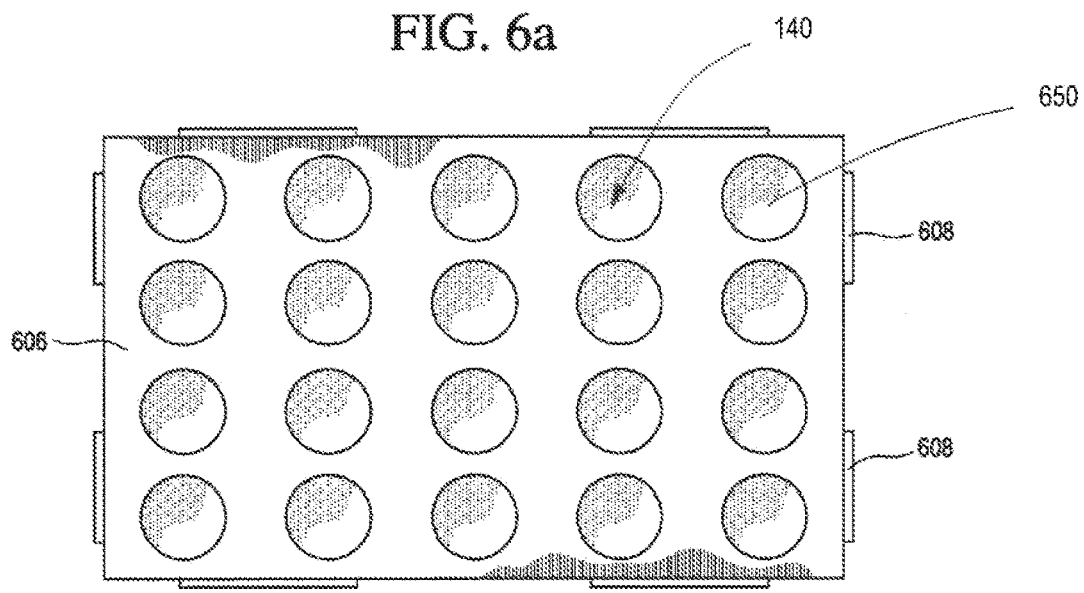
FIG. 6b is a front view of an alternative filter arrangement of a sterilization container such as a sterilization cabinet suitable for use in practicing exemplary embodiments of this disclosure.
Figure 6C:
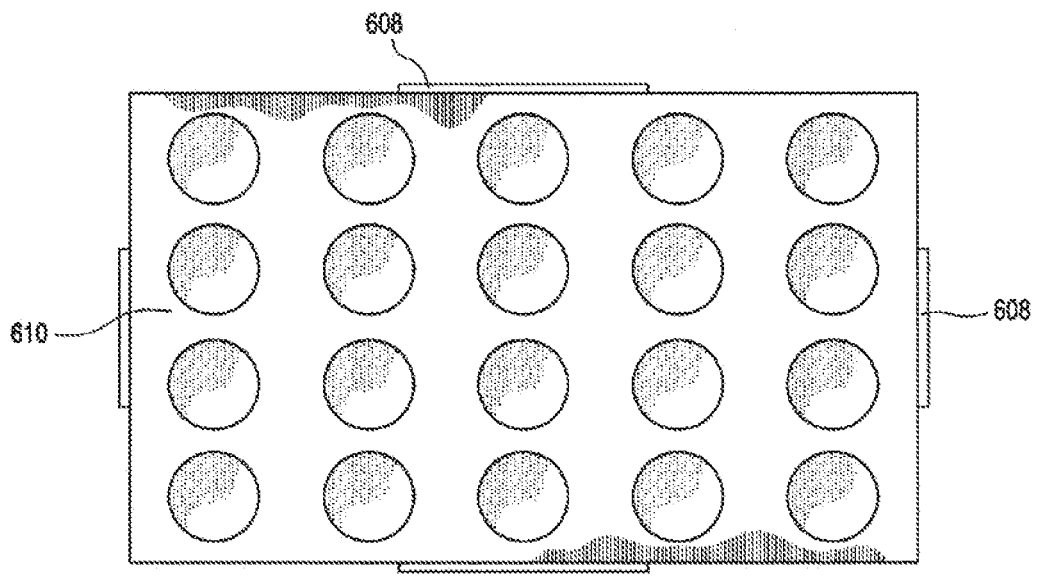
FIG. 6c is a front view of the top portion of an alternative filter arrangement of a sterilization container such as a sterilization cabinet suitable for use in practicing exemplary embodiments of this disclosure.
Figure 7A:
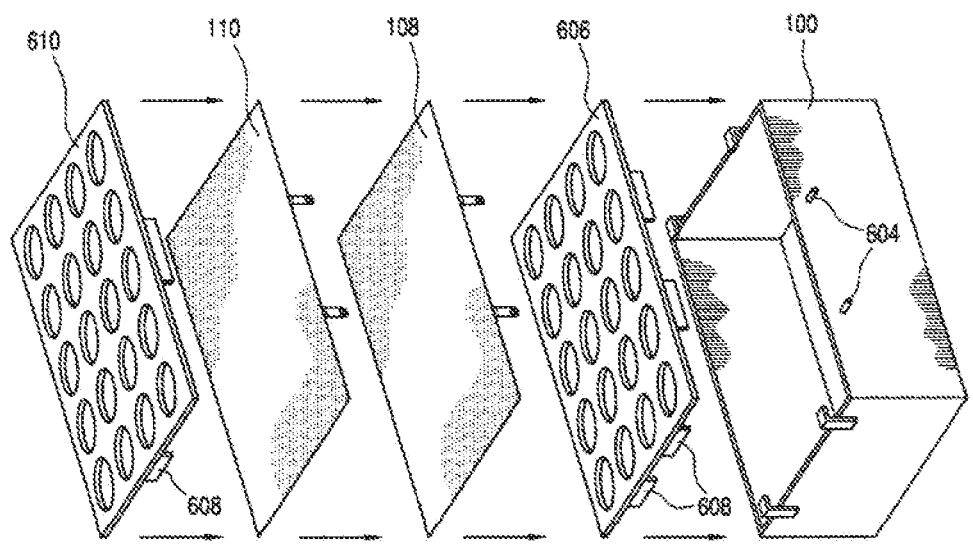
FIG. 7a is a perspective view of the separated elements of an alternative filter arrangement of a sterilization container such as a sterilization cabinet suitable for use in practicing exemplary embodiments of this disclosure.
Figure 7B:
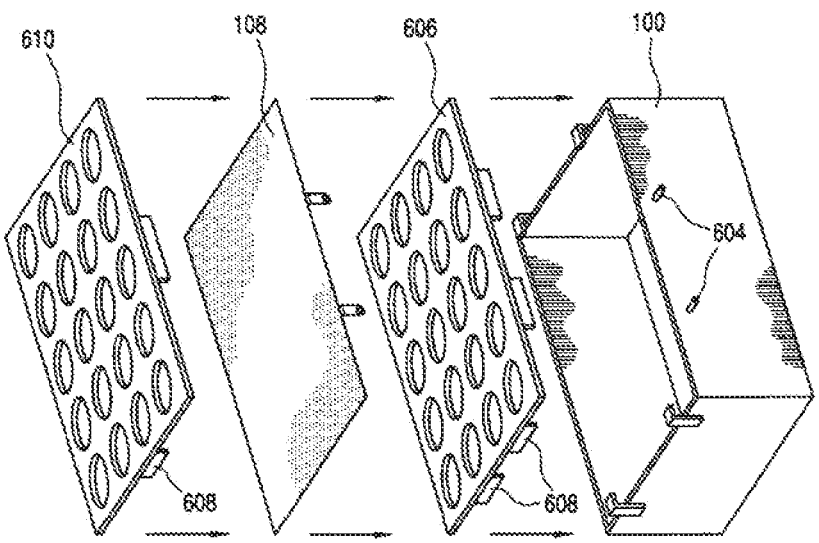
FIG. 7b is a perspective view of the separated elements of another filter arrangement of a sterilization container such as a sterilization cabinet suitable for use in practicing exemplary embodiments of this invention.
Figure 8A:
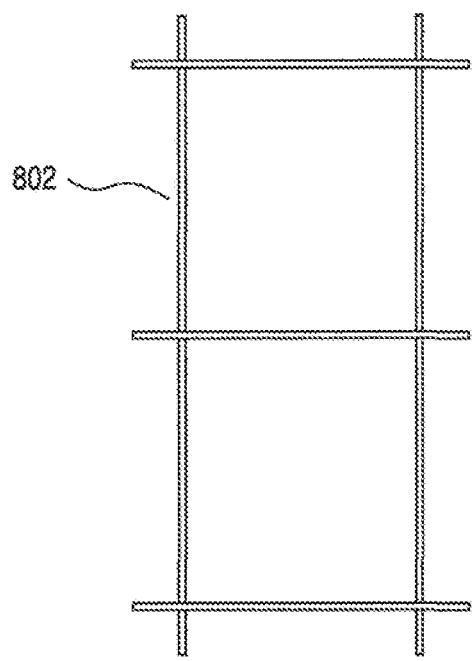
FIG. 8a is a top view of a spacer suitable for use in practicing exemplary embodiments of this disclosure.
Figure 8B:
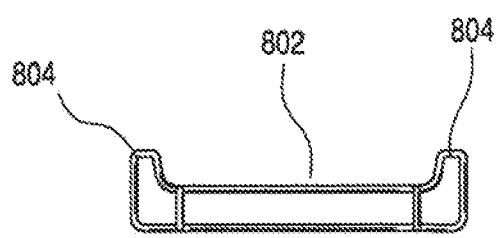
FIG. 8b is a side view of a spacer suitable for use in practicing exemplary embodiments of this disclosure.
Figure 8C:
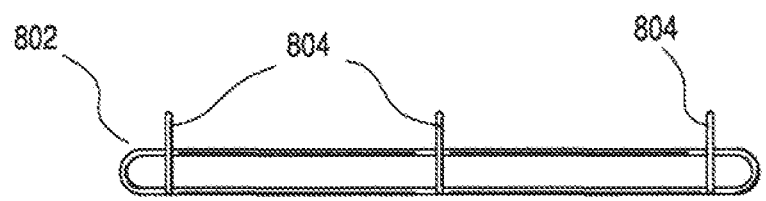
FIG. 8c is another side view of a spacer suitable for use in practicing exemplary embodiments of this disclosure.
Figure 9A:
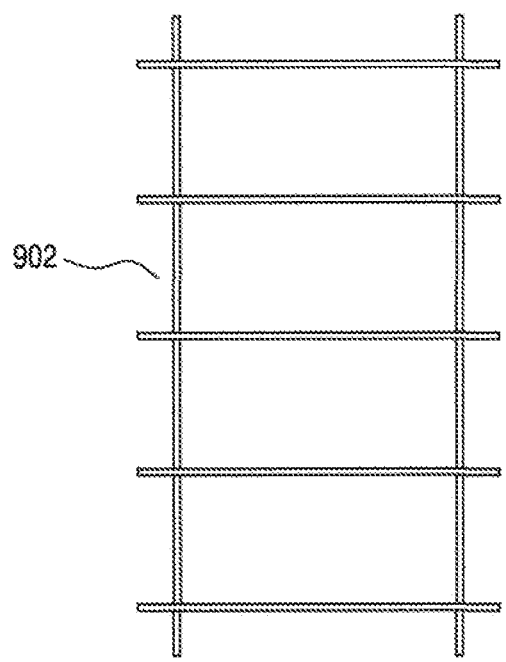
FIG. 9a is a top view of an alternative spacer suitable for use in practicing exemplary embodiments of this disclosure.
Figure 9B:
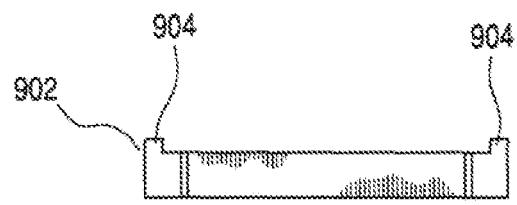
FIG. 9b is a side view of an alternative spacer suitable for use in practicing exemplary embodiments of this disclosure.
Figure 9C:
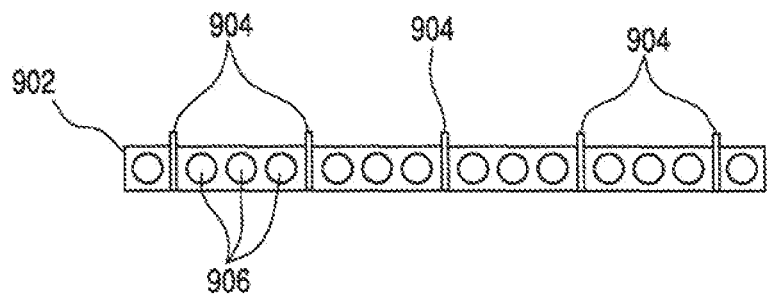
FIG. 9c is another side view of an alternative spacer suitable for use in practicing exemplary embodiments of this disclosure.
Figure 10:
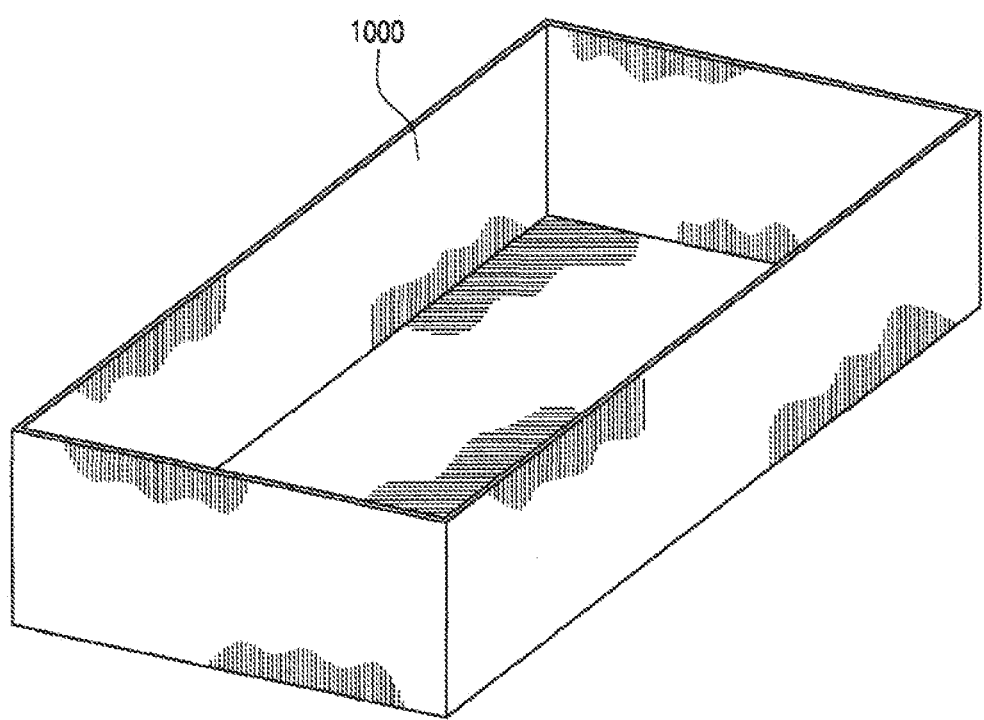
FIG. 10 is a perspective view of a sterilizing tray suitable for use in practicing exemplary embodiments of this disclosure.
Figure 11:
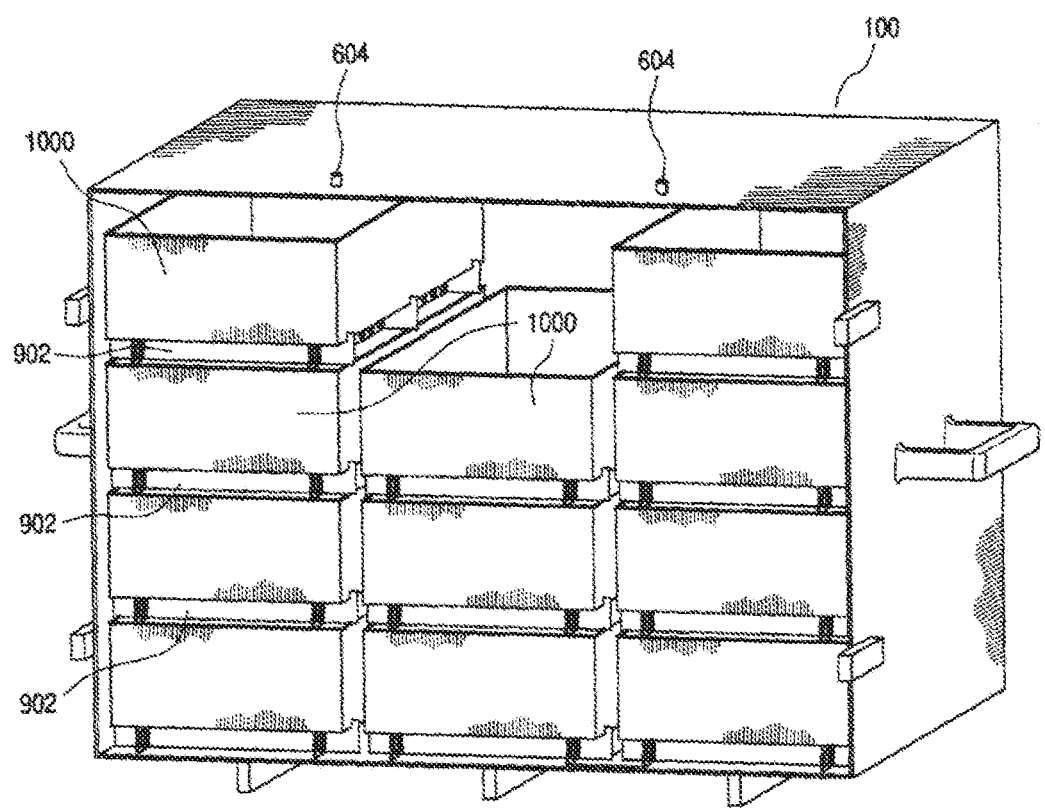
FIG. 11 is a perspective view of a sterilization container such as a sterilization cabinet suitable for use in practicing exemplary embodiments of this disclosure.
Figure 12:
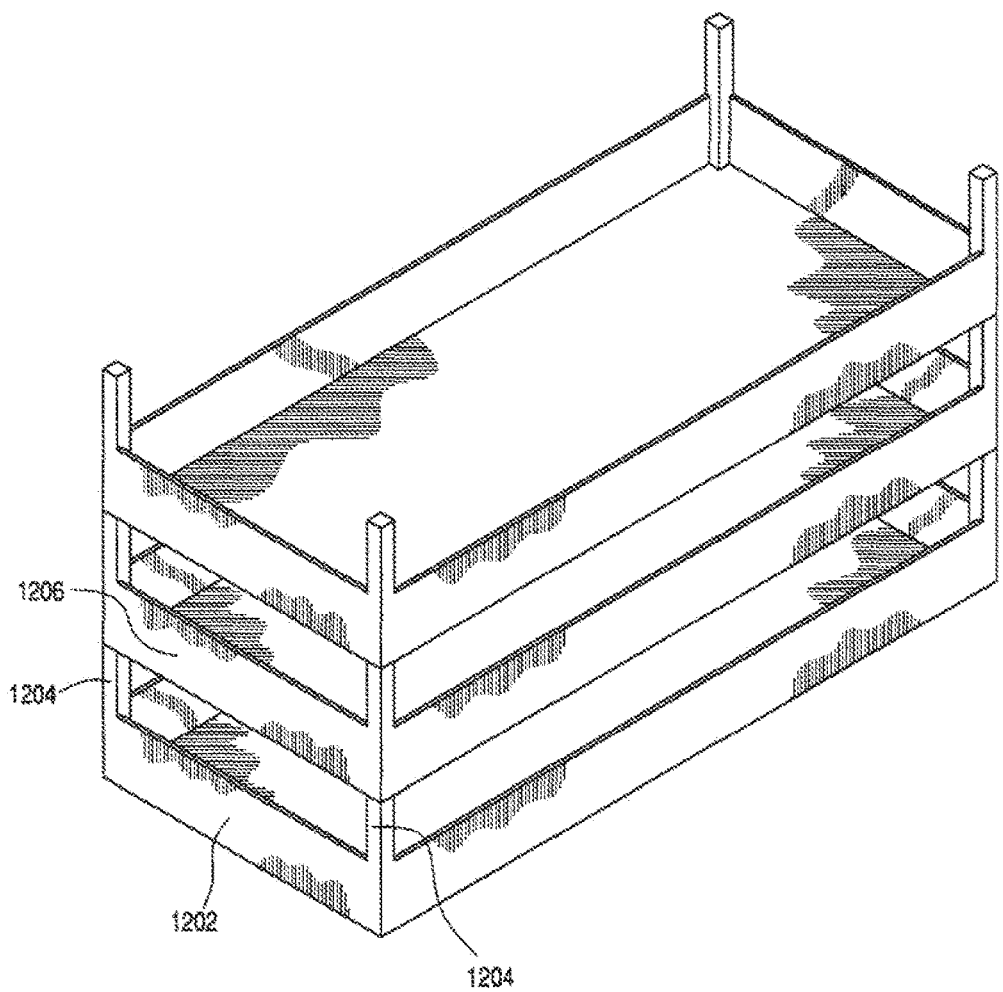
FIG. 12 is a perspective view of a pan assembly suitable for use in practicing exemplary embodiments of this disclosure.
Figure 13A:
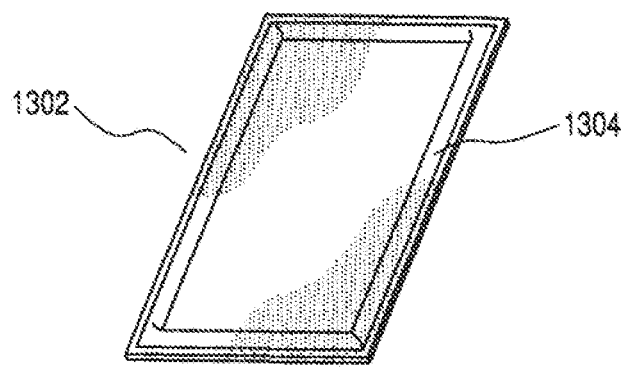
FIG. 13a is a perspective view of a filter suitable for use in practicing exemplary embodiments of this disclosure.
Figure 13B:
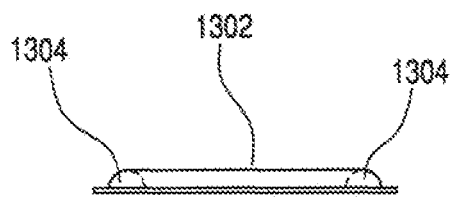
FIG. 13b is a side view of a filter suitable for use in practicing exemplary embodiments of this disclosure.
Figure 14A:
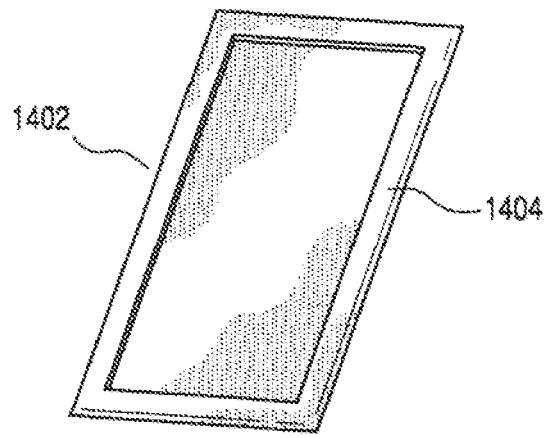
FIG. 14a is a perspective view of an alternative filter suitable for use in practicing exemplary embodiments of this disclosure.
Figure 14B:
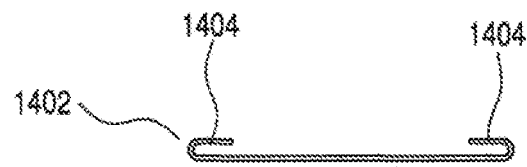
FIG. 14b is a side view of an alternative filter suitable for use in practicing exemplary embodiments of this disclosure.
Figure 15A:
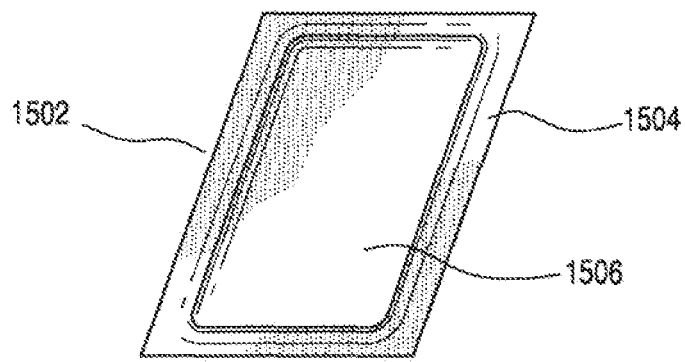
FIG. 15a is a perspective view of another filter suitable for use in practicing exemplary embodiments of this disclosure.
Figure 15B:
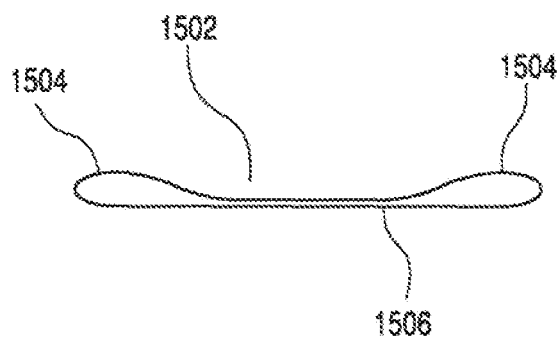
FIG. 15b is a side view of another filter suitable for use in practicing exemplary embodiments of this disclosure.
Figure 16:
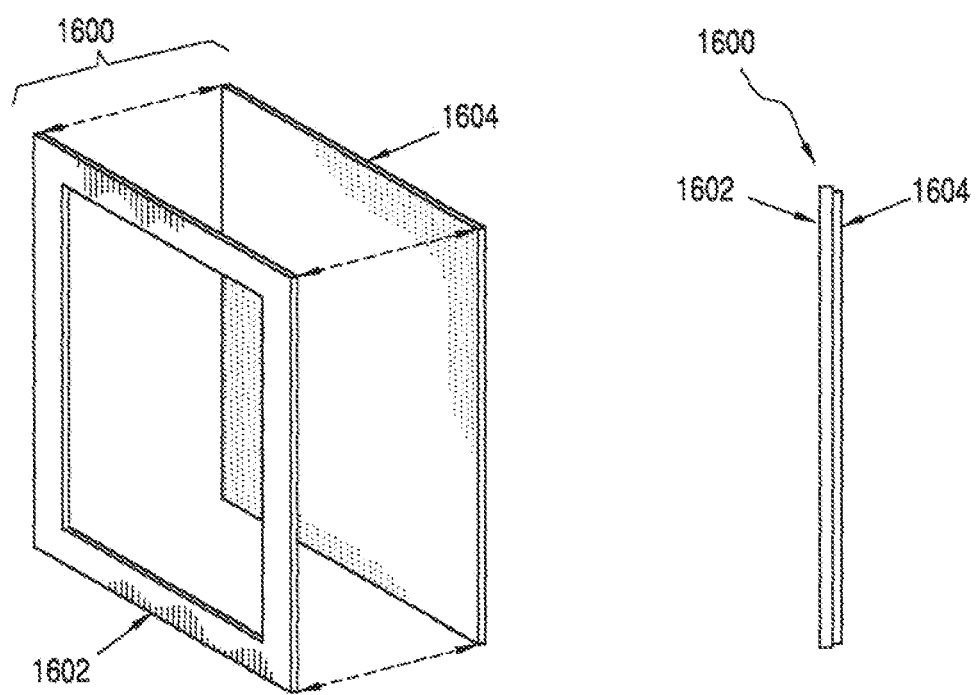
FIG. 16 is a perspective view of a filter cartridge suitable for use in practicing exemplary embodiments of this disclosure.
Figure 17:
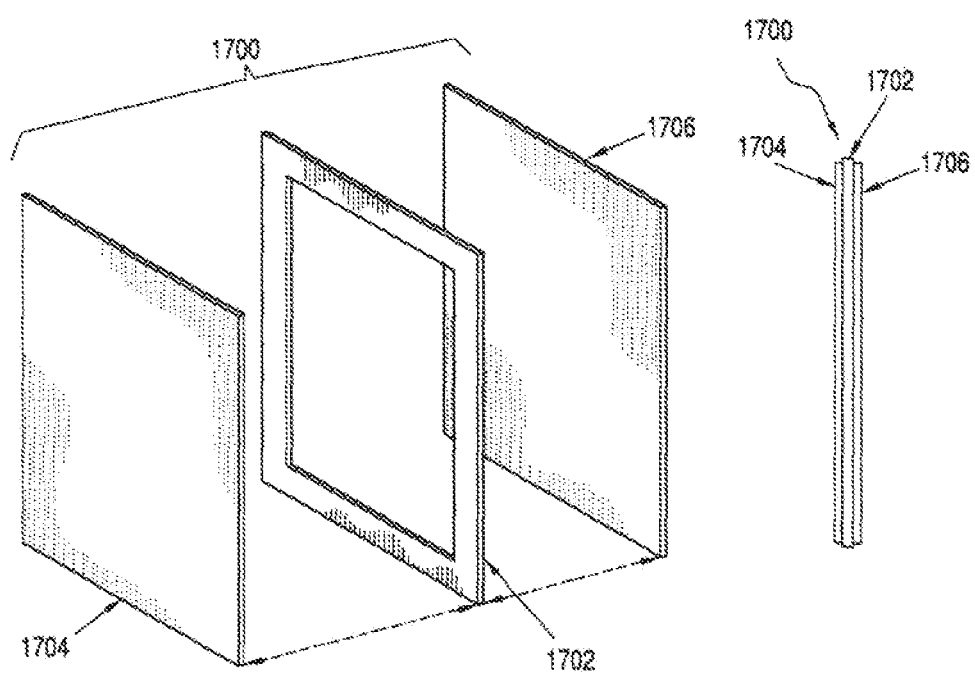
FIG. 17 is a perspective view of an alternative filter cartridge suitable in practicing exemplary embodiments of this disclosure.
Figure 18:
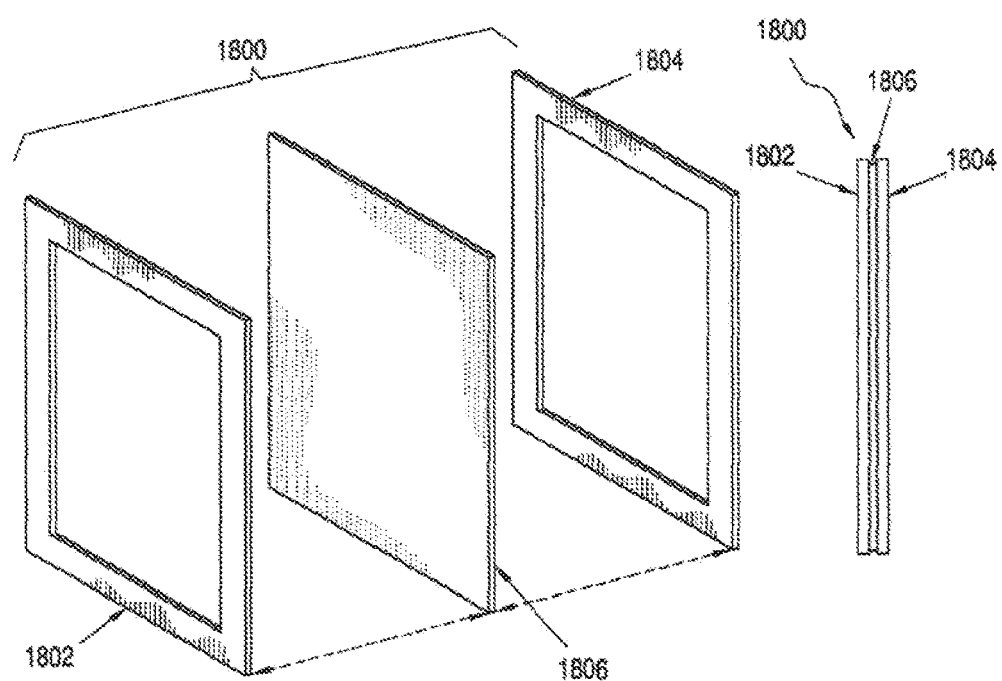
FIG. 18 is a perspective view of an alternative filter cartridge suitable in practicing exemplary embodiments of this disclosure.
Figure 19:
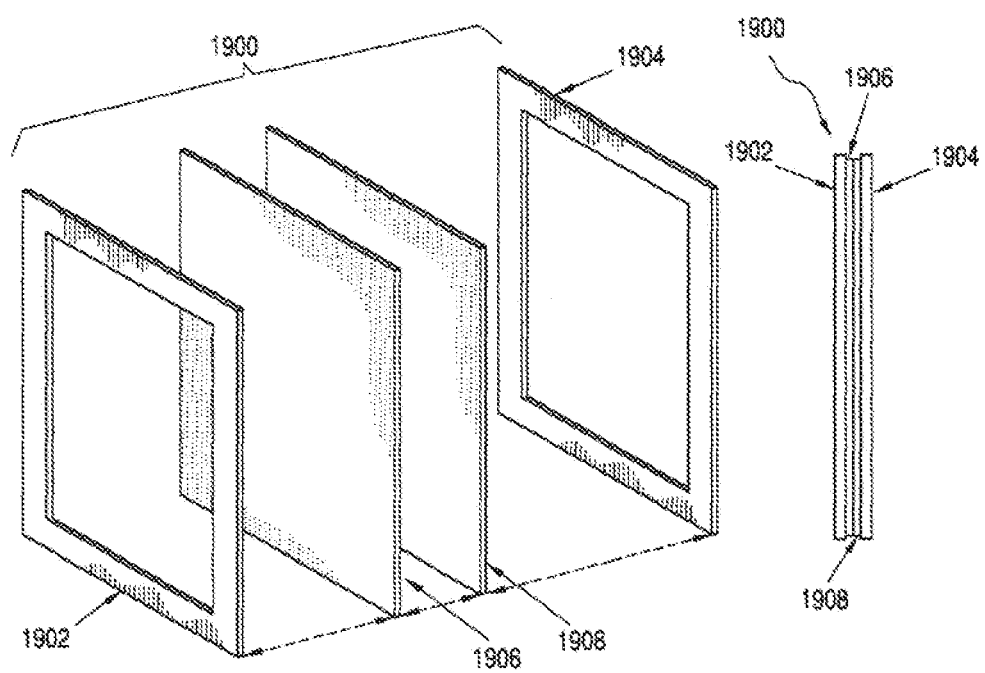
FIG. 19 is a perspective view of another filter cartridge suitable in practicing exemplary embodiments of this disclosure.
Figure 20:
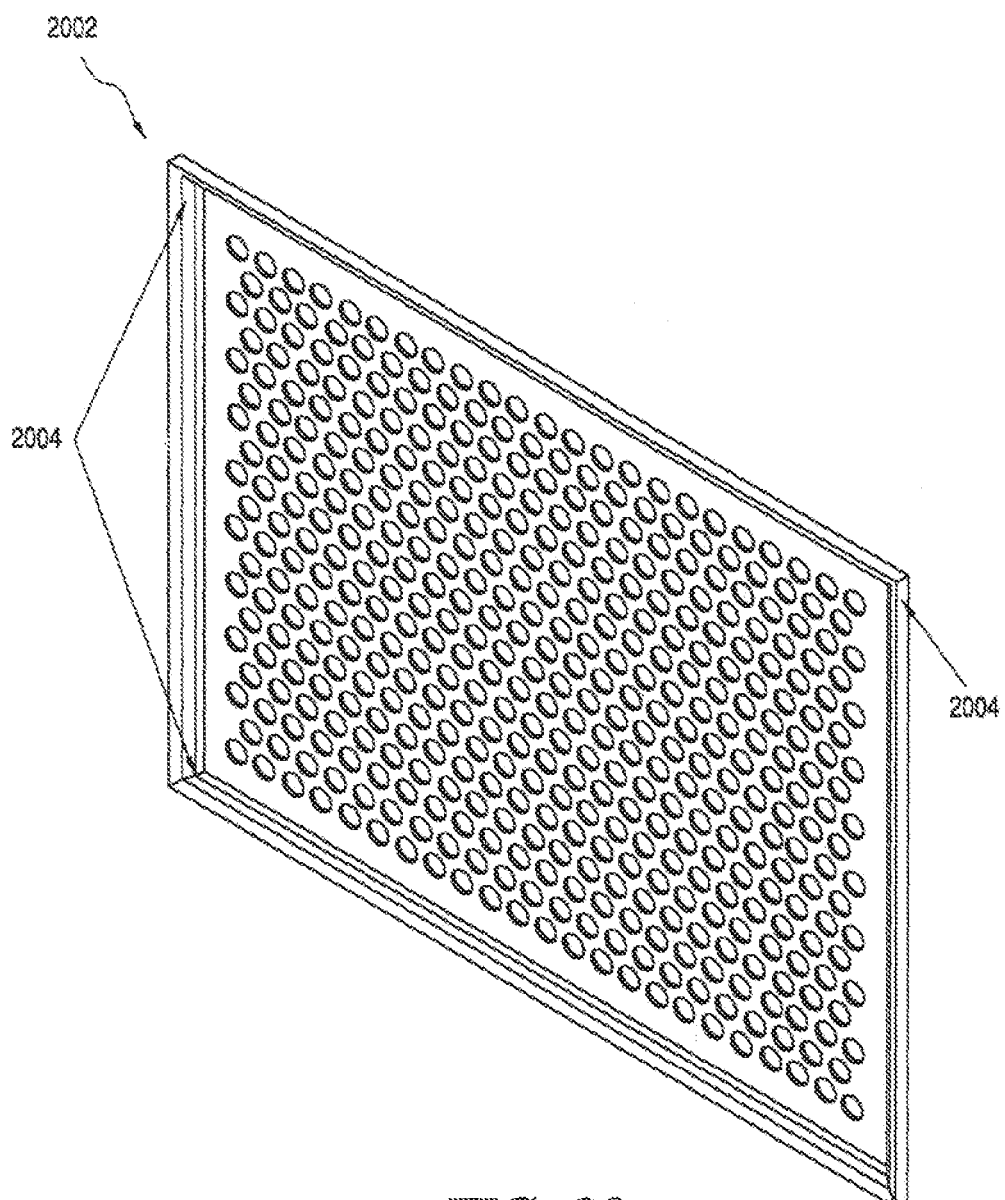
FIG. 20 is a filter cartridge holder suitable in practicing exemplary embodiments of this disclosure.
Figure 21:
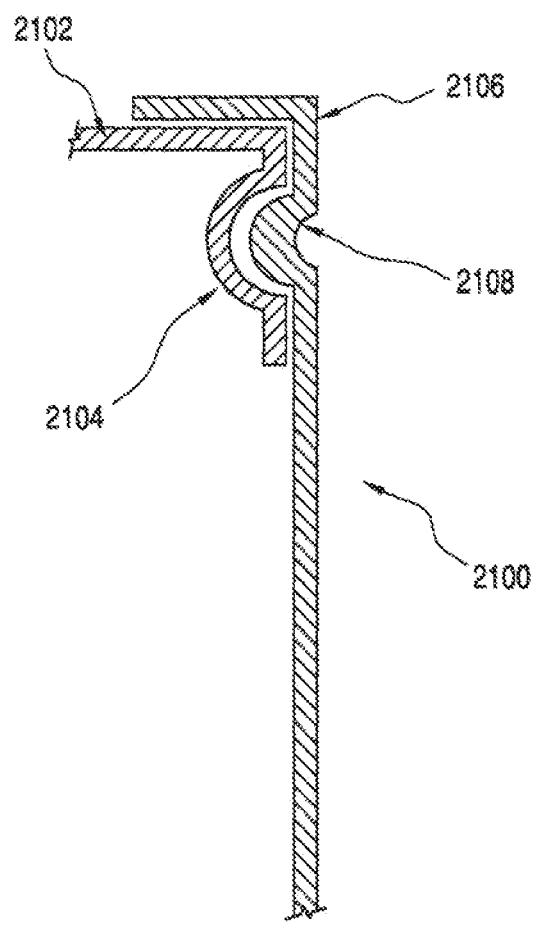
FIG. 21 is a magnified cross-sectional view of a sterilization container such as a sterilization cabinet and a filter door suitable for use in practicing exemplary embodiments of this disclosure.
Figure 22:
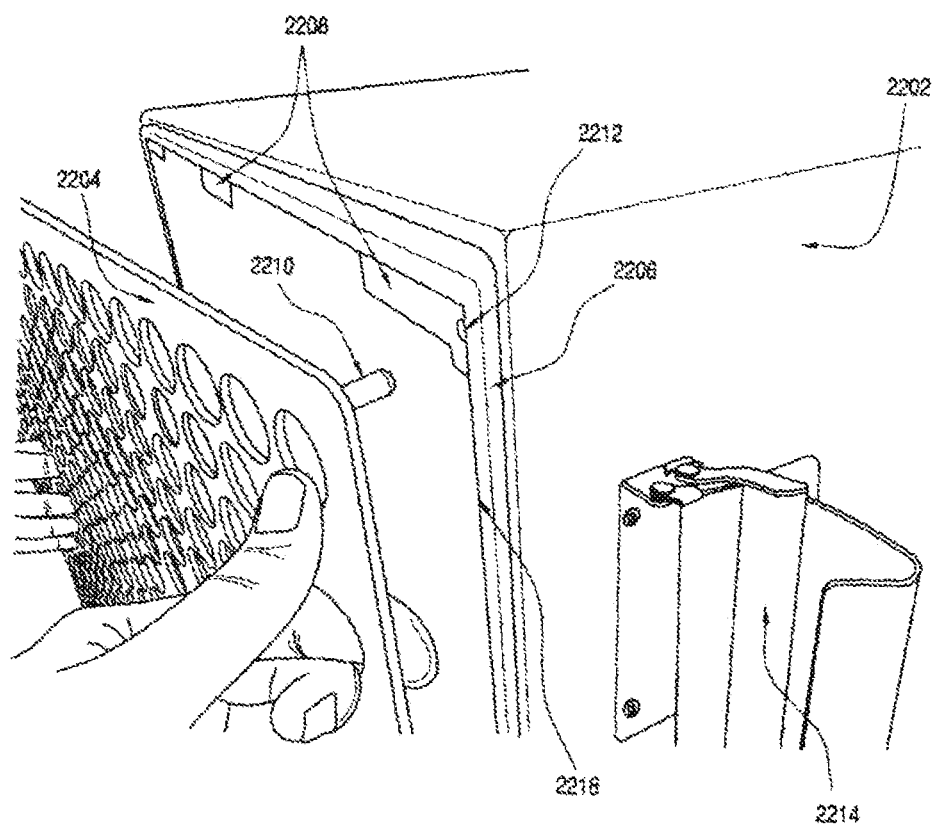
FIG. 22 is a perspective view of an exemplary a sterilization container such as a sterilization cabinet and filter door suitable for use in practicing exemplary embodiments of the present disclosure.
Figure 23:
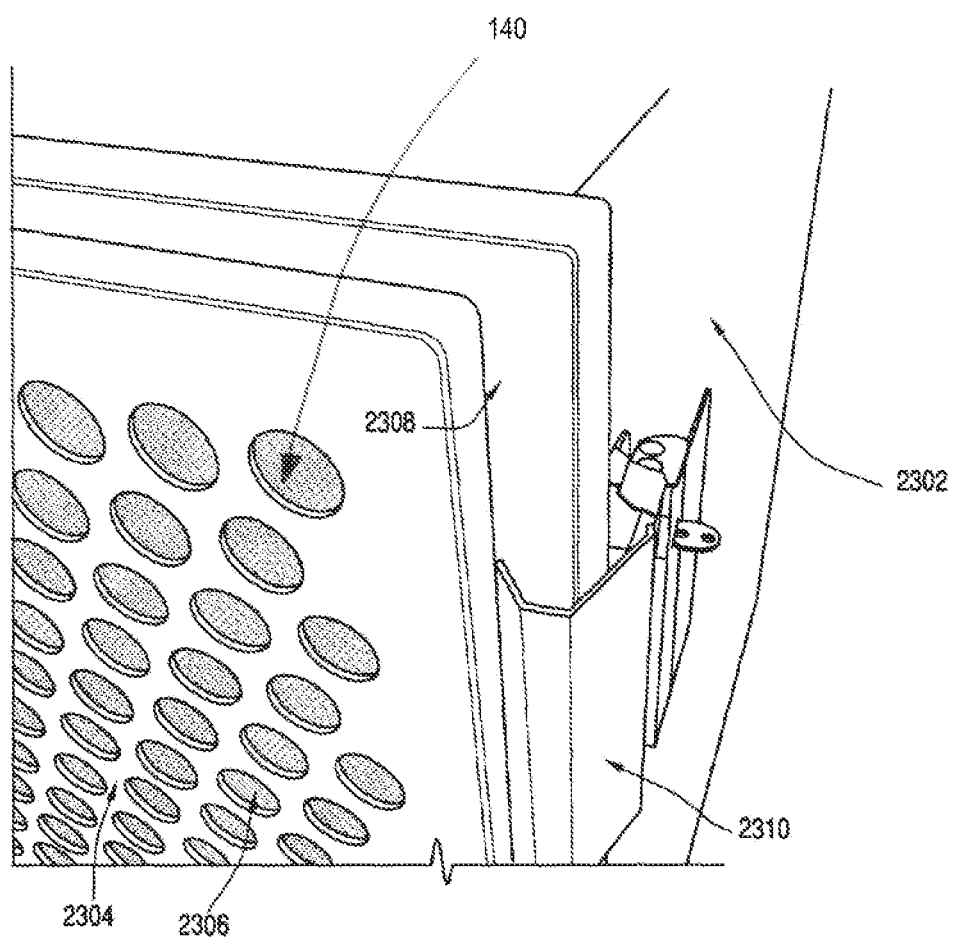
FIG. 23 is a perspective view of an exemplary a sterilization container such as a sterilization cabinet and filter door suitable for use in practicing exemplary embodiments of the present disclosure.
Figure 24:
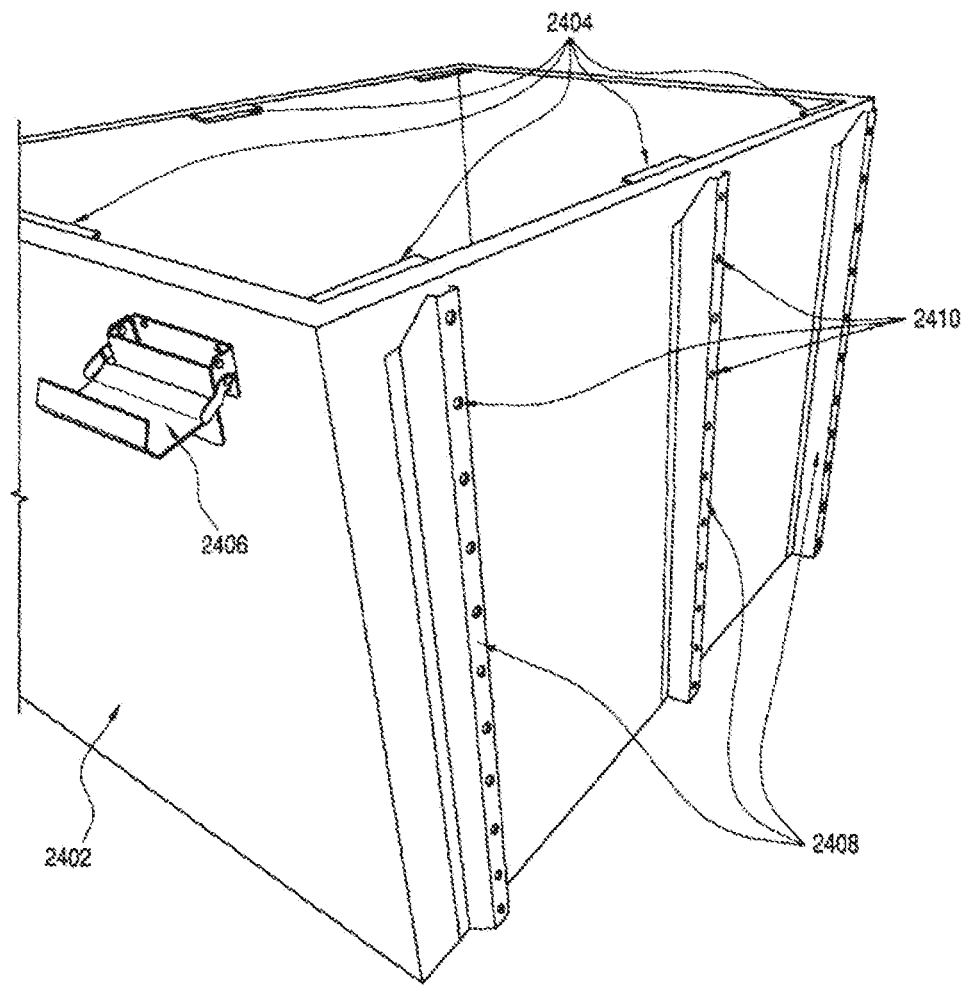
FIG. 24 is a bottom perspective view of an exemplary sterilization container such as a sterilization cabinet suitable for use in practicing exemplary embodiments of the present disclosure.
Figure 25:
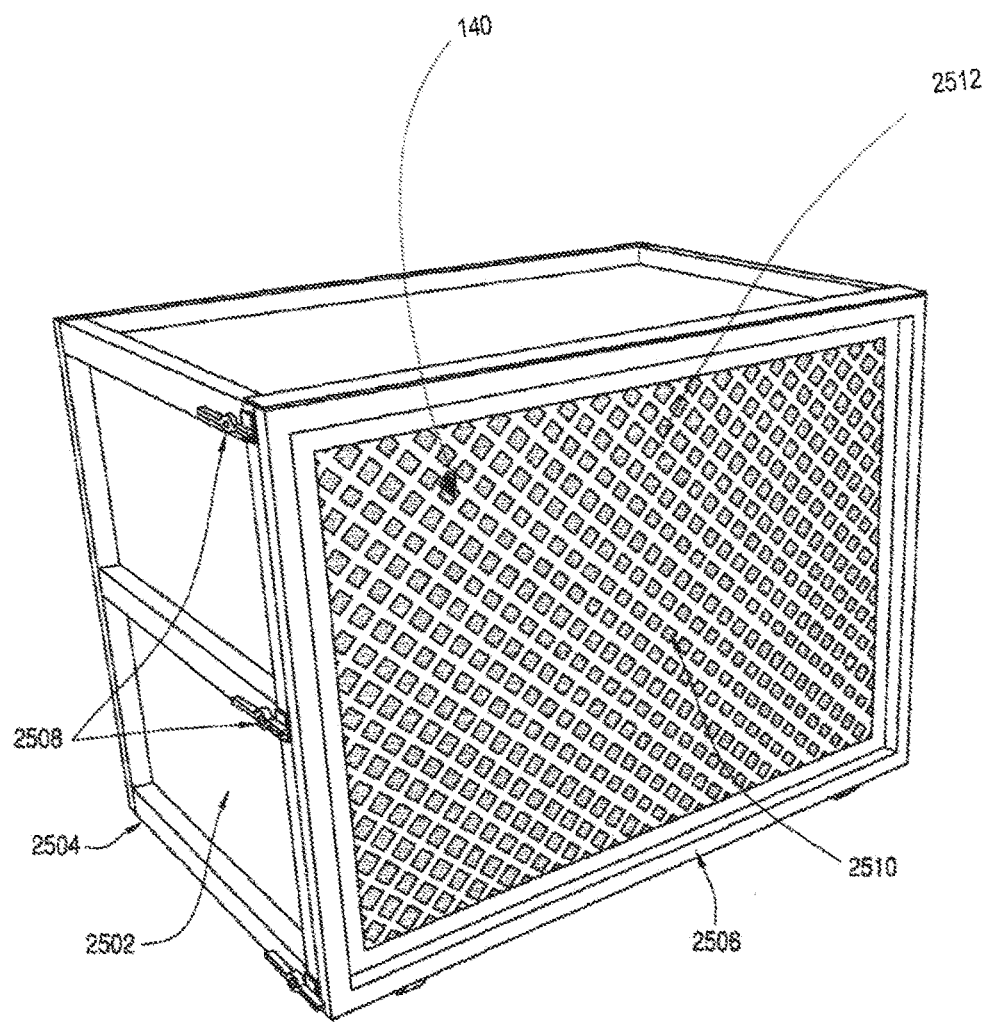
FIG. 25 is a perspective view of an alternative embodiment of a sterilization container such as a sterilization cabinet suitable for use in practicing exemplary embodiments of this disclosure.
Figure 26:
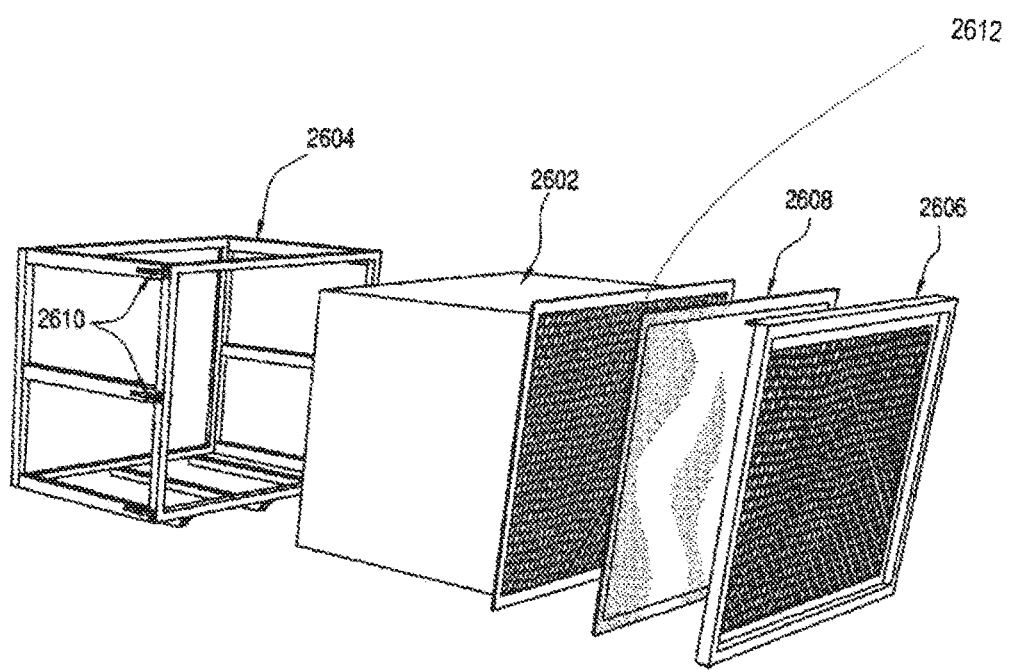
FIG. 26 is a perspective view of a separated alternative embodiment of a sterilization container such as a sterilization cabinet suitable for use in practicing exemplary embodiments of this disclosure.

In yet another exemplary embodiment, as shown in FIGS. 6a-6c, the sterilization cabinet 100 includes sterilization cabinet frame 112, bars 602 and hooks 604. In this configuration, there is no front side of sterilization cabinet 100 in front of bars 602. It should be appreciated that exemplary embodiments of sterilizing cabinet 100 also include embodiments of sterilization cabinet 100 that do not contain bars 602. In yet another exemplary embodiment of sterilization cabinet 100, bars 602 are removeable such that bars 602 can be removeably affixed to sterilization cabinet 100 when desired. FIG. 6b illustrates filter door 606 which contains primary filter 106. In exemplary embodiments filter door 606 covers the front opening of sterilizing cabinet 100 in FIG. 6a. Filter door 606 clamps onto sterilization cabinet 100 with clamps 608. Bars 602 prevent the contents of sterilization cabinet 100 (typically a tray containing instruments for sterilization) from ripping or breaking primary filter 108 and secondary filter 110.

FIG. 6c illustrates a second filter door 610, which attaches to filter door 606 and sterilizing cabinet 100 with the use of clamps 608. In this configuration, it can be appreciated that clamps 608 on filter door 610 fit into the spacing between clamps 608 on filter door 606. This arrangement prevents the clamps 608 from filter door 606 from interfering with clamps 608 from filter door 610. Additionally, since filter door 610 is attached independently from filter door 606, secondary filter 110 can be removed with filter door 610 after a sterilization cycle has completed without disturbing filter door's 606 seal with sterilization cabinet 100. Each filter door 606, 610 includes a plurality of holes or openings 650 for the passage of sterilizing steam or heat. Although holes or openings are shown, it should be appreciated that any type of opening can be used, including but not limited to holes, slits, diamonds, or fenestrated openings as long as the available area for the ingress and egress of a gas to and from the interior volume of the sterilizing cabinet 100 provides the desired venting pass through area to volume ratio. Further, it should be appreciated that, although the plurality of holes 650 of filter door 606 and filter door 610 in the configuration shown in FIGS. 6b and 6c will align, such alignment is not necessary. The venting pass through area to volume ratio is based on the venting pass through area 140 of the primary filter 108 and first door 606 and not both doors. It should be appreciated that the gas passing through the secondary filter 110 will be dispersed into a flow path that may be different than the flow path through the holes 650 of the first door 606.

In this embodiment, filter door 606 forms a seal with sterilization cabinet 100 at the edges of the open portion of the sterilization cabinet frame 112, such that any sterilizing steam that enters or exits sterilizing cabinet 100 during a sterilization cycle must pass through filter door 606 and primary filter 106. Likewise, filter door 610 forms a seal with filter door 606 such that any sterilizing steam that exits sterilizing cabinet 100 and primary filter 108 must pass through filter door 610 and secondary filter 110. As shown in FIG. 6b, the filter door 606 includes holes or openings 650 and defines a venting pass through area 140 of the sterilization cabinet 100. The sterilizing cabinet 100 as shown in FIG. 6b having 20 holes within the door 606 having dimensions of approximately 34 inches by 24 inches includes a venting pass through area of approximately 240 inch$^2$ based on each hole having an area of approximately 12 inch$^2$. The total volume of the sterilization cabinet 100, wherein the length is approximately 34 inches, the width is approximately 22 inches, and the height is approximately 24 inches, is approximately 17,952 inches$^3$. Thus, the sterilization cabinet 100 as shown in FIG. 6b would have a venting pass through area to volume ratio of approximately 0.01 inch$^2$ per inch$^3$.

Alternatively, for the sterilization container of FIG. 6b, being 24 inch by 11 inch by 11 inch, the venting pass through area to volume ratio of approximately 0.08 inch$^2$ per inch$^3$ is obtained, that is 2 square inches per 25 cubic inches. Similarly, for the sterilization container of FIG. 6b, being 34 inch by 30 inch by 30 inch, the venting pass through area to volume ratio of approximately 0.008 inch$^2$ per inch$^3$ is obtained.

Exemplary embodiments of sterilization cabinet 100 can include one or more vents so long as the venting pass through area to volume ratio is equal to or greater than 0.008 inch$^2$ per inch$^3$, or 1 square inch:125 cubic inches, and in select configurations between 0.02-0.2 inch$^2$ per inch$^3$, or between 1 square inch:50 cubic inches and 1 square inch:5 cubic inches, and in further configurations between 0.16-0.2 inch$^2$ per inch$^3$, or 4 square inches:25 cubic inches and 1 square inch:5 cubic inches.

The high venting pass through area to volume ratio reduces the drying time required after the sterilization cycle. The sterilization cabinet 100 can hold multiple trays holding instruments and, because of the venting pass through area to volume ratio, have a drying time of less than 30 minutes, and more specifically, between 10-15 minutes, and even more specifically 10 minutes. In select configurations, the drying time can be as little as 5 minutes. In one configuration, the sterilization cabinet 100 holds up to 15 trays, each tray holding up to 25 lbs. In a configuration of the disclosure, the drying time of less than 30 minutes includes multiple trays loaded into the sterilization cabinet 100, the trays holding a total of 140 lbs or less.

In another exemplary embodiment, as shown in FIGS. 20-25, the sterilization cabinet 2202, 2502, 2602, is a rigid container having an enclosing wall such as a plurality of walls and a door 2002, 2100, 2204, 2304, 2512, and 2612 defining an interior volume. The sterilization cabinet 2202, 2502, 2602, further includes at least one wall or door defining a venting pass through area 140. A filter 2510, 2306, 1302, 1402, 1502, 1602, and 1700 may occlude the venting pass through area 140. The sterilization cabinet 2202, 2502, and 2602 is constructed of 304 stainless steel with an anodized aluminum filter housing/door. The sterilization container 2202, 2502, 2602, however, can be constructed of other types of stainless steel, or other types of materials as well.

The sterilization cabinet 2202, 2502, 2602 may have a fenestrated door 2506, 2612 holding a filter 2510, 2306, 1302, 1402,1502, 1602, 1700. In one configuration, the filter 2510, 2306, 1302, 1402, 1502, 1602, 1700 is a single-use filter. The sterilization cabinet 2202 2502, 2602 is designed to be used in a steam autoclave and may hold multiple open trays containing surgical instruments. Trays within the container 2202, 2502, 2602 may be separated by spacers 902 having dividers or lips 904 along the edges of spacer 902 and throughout the midsection of spacer 902 to ensure separation and maximum steam exposure. The sterilization cabinet 2202, 2502, and 2602 has been validated to sterilize 375 lbs. of instruments along with the spacers 902. The validation was conducted with 15 instrument trays at 25 lbs. Actual expected loads in hospital settings are likely to be less. For example, loads in a hospital setting are more typically 140 lbs or less, and even more typically approximately 110 lbs. It should be appreciated that sterilized instruments can be stored for up to 30 days within the closed (intact filters) sterilization container.

The sterilization cabinet 2202, 2502, 2602 is loaded into the sterilizer, for example, an autoclave, with a transfer carriage (not shown).

The use of a single-use disposable filter cartridge 1302, 1402, 1502, 1602, 1700 installed in the fenestrated door 2506, 2612 eliminates the need for a sealed gasket found on prior systems. The omission of a reusable gasket eliminates contamination risks due to failed reusable gaskets. It is understood the single use disposable filter can be used with a separate or integral cartridge.

The sterilization cabinet 2202, 2502, 2602 is indicated for enclosing other medical devices that are to be sterilized by a healthcare provider. It is intended to allow sterilization of the enclosed materials and maintain sterility for up to 30 days until used. The sterilization cabinet 2202, 2502, 2602 is intended to be used in pre-vacuum steam sterilizers with a prevacuum cycle of 270° F. (132° C.) and exposure time of 4 minutes. The sterilization cabinet 2202, 2502, 2602 is intended to be used with Turbett Surgical filters.

Validation was done using three trays per level and a maximum instrument load of 25 lbs. per tray. The validation load included six 1 mm×500 mm lumens and six 3 mm×400 mm lumens. The total weight of instruments and trays validated is 375 lbs. The trays holding instruments within the sterilizing cabinet 100 were uncovered, perforated or wire mesh general delivery trays.

The principal material of construction of the sterilization cabinet 2202, 2502, 2602 may be stainless steel and aluminum. However, it should be appreciated that other materials may be used. In one configuration, the overall size is 34"×24"×22". The empty container 210 weighs approximately 136 lbs. It is thus a relatively large container, typically associated with a transfer cart. In this configuration, the venting pass through area includes 905 holes, each having a diameter of approximately 0.74 inches, thus providing a venting pass through area of 398.2 (approximately 400) square inches. Thus, in an exemplary embodiment, the where the volume is approximately 17,952, cubic inches based on the overall size, the venting pass through area to volume ratio is approximately 0.022 inch$^2$ per inch$^3$ or 11 square inches:500 cubic inches. If internal dimensions provide a volume of approximately 14,846 cubic inches, the venting pass through area to volume ratio is approximately 0.027 inch$^2$ per inch$^3$ or 27 square inches:1000 cubic inches. It should be appreciated that exemplary embodiments of the sterilization cabinet can be other dimensions, shapes and sizes that provide similar vent to volume ratios, wherein the ratio is at least approximately 0.022 inch$^2$ per inch$^3$ or 11 square inches:500 cubic inches, and in select configurations between 0.008-0.21 inch$^2$ per inch$^3$, (1 square inch:125 cubic inches and 21 square inches:100 cubic inches) and in further configurations, between 0.16-0.2 inch$^2$ per inch$^3$ (4 square inches:25 cubic inches and 1 square inch:5 cubic inches). That is, the sterilization container, such as the cabinet may be configured of any shape or size so long as the venting pass through area has dimensions corresponding to the volume to provide the desired vent area to volume ratio. Similarly, the venting area may have many shapes, sizes and/or locations on the sterilization cabinet, so long as the venting area and volume meet the vent pass through area to volume ratios.

Technological Characteristics:

The sterilization cabinet 2202, 2502, 2602 has been validated to sterilize 375 lbs. of instruments along with the spacers 902. The validation was conducted with 15 instrument trays at 25 lbs. each to represent the most challenging case. The validations included thermal profile, sterilization efficacy, and drying in a pre-vacuum steam sterilizer. Sterilized instruments can be stored for up to 30 days within the closed container.

The sterilization cabinet 2202, 2502, 2602 is constructed of 304 stainless steel sheet metal on a rigid stainless steel frame. The sterilization container, such as the cabinet opens from the side for easy placement and retrieval of surgical trays. In one configuration, a sidewall is omitted to define a door way or opening to the cabinet for inserting and removing trays (medical instruments). A filter 1700 comprised of 1 or 2 layers of filter paper 1704, 1706 and a compressible gasket 1702 is placed between the door and the cabinet, such that a portion of the filter or gasket is disposed between the door and the cabinet to form a sealed interface. After use (the sterilization process and removal of the trays (the sterilized medical instruments), the filter 1700 having the compressible gasket 1702 is discarded.

The following testing was conducted to establish substantial equivalence and efficacy:
ANS/AAMI ST77: Containment Devices for Reusable Medical Device Sterilization testing:
  Pre-vacuum thermal profile
  Steam pre-vacuum sterilization efficacy
  Pre-vacuum dry time
  Microbial aerosol challenge
  30 day shelf-life study
AAMI TIR 30: A Compendium of Processes, Materials, Test Methods and Acceptance Criteria for Cleaning Reusable Medical Devices testing:
  Protein analysis and Total Organic Carbon Manual cleaning methods
ANS/AAMI HE75: Human Factors Engineering—Design of Medical Devices testing:
  Human factors usability study Turning now to FIG. 25, the sterilization cabinet 2202 includes door 2204 having a large vented area 2512. In one configuration, the venting pass through area of the door 2204 includes a plurality of holes or a fenestrated grid throughout its center. For example, the venting pass through area 2512 of the door 2204 includes approximately 461 holes, each having an area of approximately 0.82 square inches, thus providing a venting pass through area 2512 of 377 inch. The sterilization cabinet 2202 having an interior volume of approximately 17,952 inch$^3$ would thus, have a venting pass through area of 377 inch$^2$ compared to a volume of 17,952 inches$^3$, or a ratio of approximately 0.021 inch$^2$ per inch$^3$ or 21 square inches:1000 cubic inches.

Exemplary embodiments of sterilization cabinet 2202 can include a single vent or a plurality of vents to define the venting pass through area, so long as the venting pass through area to volume ratio between 0.008-0.21 inch$^2$ per inch$^3$ (or 1 square inch:125 cubic inches and 21 square inches:1000 cubic inches) and in select configurations between 0.16-0.21 inch$^2$ per inch$^3$ (or 4 square inches:25 cubic inches and 21 square inches:1000 cubic inches), or in further configurations equal to or greater than 0.021 inch$^2$ per inch$^3$ or 21 square inches:1000 cubic inches.

The high venting pass through area to volume ratio reduces the drying time required after the sterilization cycle. That is, assuming multiple trays of medical instruments in a sterilization cabinet 100, for example, up to 15 trays, are placed in a sterilizer device, such as an autoclave, the sterilization cabinet 2202, with the venting pass through area to volume ratio of 0.021 per inch, would require a dry time of less than 30 minutes, and more specifically approximately 10-15 minutes, and even more specifically, 10 minutes. In one configuration, a dry time of less than 15 minutes is provided when a ratio of the venting pass through area to the interior volume of the sterilization cabinet 2202 is between 0.008-0.21 inch$^2$ per inch$^3$ (or 1 square inch:125 cubic inches and 21 square inches:1000 cubic inches). In another configuration, the drying time is approximately 10 minutes for up to 140 lbs of medical instruments arranged in the sterilization cabinet 2202 on multiple trays.

In one configuration, the sterilization container has dimensions of approximately 34 inch by 22 inch by 24 inch and the door has 869 holes at 0.766" diameter and 32 holes at 0.5" diameter. Thus, the vented pass through area is 400 inch$^2$ plus approximately 6 inch$^2$. Thus, the ratio of the venting pass through area to the interior volume of the sterilization cabinet is approximately 406 inch$^2$ to 17952 inch$^3$ or 0.0226 inch$^2$ per inch$^3$.

Figure 27:
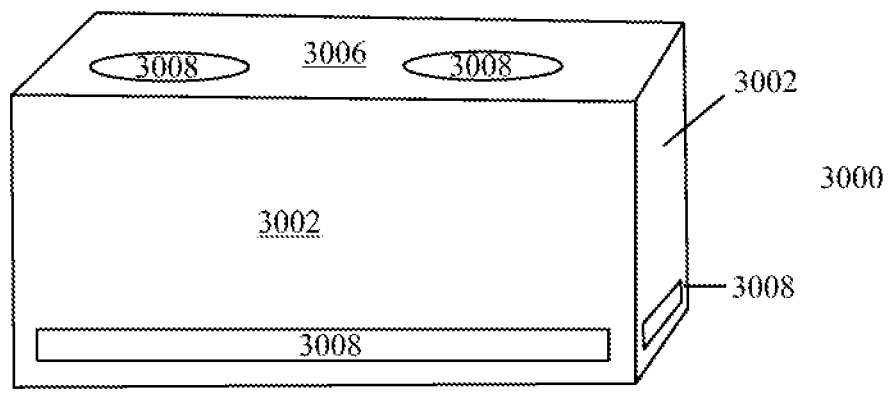
FIG. 27 is a perspective view of an alternative embodiment of a sterilization container such as a sterilization cabinet suitable for use in practicing exemplary embodiments of this disclosure.
Figure 28:
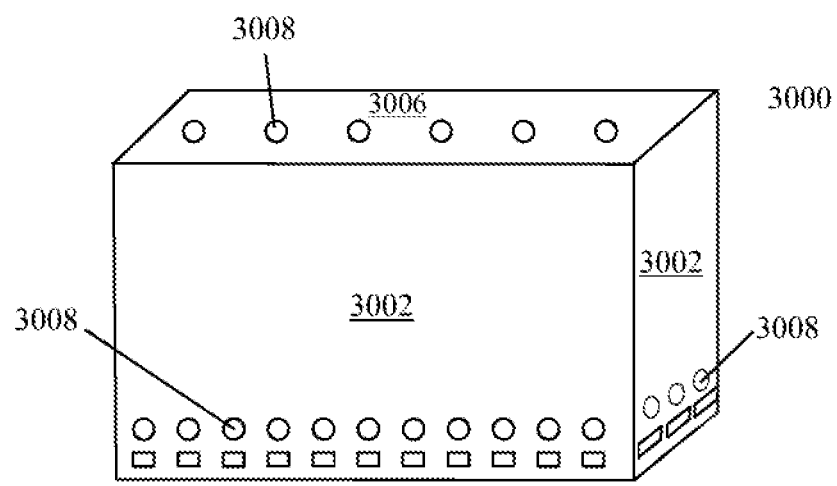
FIG. 28 is a perspective view of yet another alternative embodiment of a sterilization container such as a sterilization cabinet suitable for use in practicing exemplary embodiments of this disclosure.

As shown in FIGS. 27 and 28, the sterilization cabinet 3000 includes a plurality of sidewalls 3002 and a door (not shown). The sterilization cabinet 3000 can hold multiple trays for holding medical instruments. In one configuration, the sterilizing cabinet 3000 can hold up to 15 trays. At least one of the sidewalls 3002 includes a large vented area. For example, as shown in FIGS. 27 and 28, walls 3002 include a vented portion 3008 along the lower portion of the walls and a vented portion along top walls 3006. The vented portion 3008 may include a large vent, or multiple vents of any shape and size that provide the venting pass through area to volume ratio. In one configuration, the vented portion 3008 includes rectangular vents along a lower portion of the sidewalls 3002 and smaller oval or circular vents along top wall 2006. It should be appreciated that the vents 2008 along the lower portion of walls 3002 may permit drainage of condensate to further decrease the amount of dry time required during the sterilization process.

In one configuration, the total venting pass through area 3008 of the sidewalls 3002 and top wall 3006 to the interior volume of the sterilization cabinet 3000 ratio is greater than 0.008 inch$^2$ per inch$^3$. The high venting pass through area to volume ratio is sufficient to provide a dry time of 30 minutes or less, and more preferably 15 minutes, and even more preferably 10 minutes. In one configuration, these drying times are achieved when 140 lbs of medical instruments are loaded on trays in the sterilization cabinet 3000. The venting pass through areas 3008 of the sterilization cabinet 3000 may be smaller or larger, of a different shape, or provided on a different location of the sidewalls, top wall, bottom wall, and/or door, or include a plurality of holes or a fenestrated grid throughout its center, provided, however, that the venting pass through area to volume ratio is greater than 0.008 inch$^2$ per inch$^3$ (or 1 square inch:125 cubic inches).

The present system is distinguished from prior trays which were wrapped with filter media, then disposed in an autoclave and transported to the surgical field after the sterilization process, in that there is no sterilizing container having a plurality of sidewalls and an opening for receiving an instrument tray, with a filter occluding a venting pass through area and the ratio of venting pass through area to volume of the sterilizing container being at least 0.008 inch$^2$ per inch$^3$ (or 1 square inch:125 cubic inches) and in further configurations the ratio being from 0.16 to 6 inch$^2$ per inch$^3$ (or 4 square inches:25 cubic inches to 6 square inches:1 cubic inch).

Further, the sterilization container of the present system can accommodate trays with instruments or devices in the tray, wherein the instruments or devices may or may not be wrapped with filter paper and the tray may or may not be wrapped with filter paper. Thus, it is contemplated the sterilization container can retain unwrapped trays with instruments or devices, wrapped trays with instruments or devices, unwrapped instruments or devices as well as wrapped instruments or devices wherein the ratio of the venting pass through area to volume of the sterilization container provides drying times less than 30 minutes and in select configurations less than 15 minutes after the sterilization cycle.

While select configurations may include a drain for passing condensate from the interior of the sterilization container, it is contemplated that other configurations having the present ratio of venting pass through area to volume can provide the reduced drying time (such as 10 minutes) without draining the condensation. In a further configuration, the floor of the sterilization container can be configured to collect or pool condensation within the container.

What is claimed is:

1. A sterilization container for retaining surgical instruments in a sterilizer, the sterilization container comprising:
   (a) a top wall, a bottom wall, a rear wall, a right sidewall and a left sidewall of the sterilization container and a door defining an interior volume sized to receive a plurality of instrument trays, each instrument tray sized to retain a plurality of medical instruments, wherein each of the top wall, bottom wall, rear wall, right sidewall and left sidewall is an enclosing wall, and wherein an opening extends between the left sidewall and the right sidewall and between the top wall and the bottom wall and lying in a plane spaced from the rear wall, and wherein the opening is sized to pass the plurality of instrument trays;
   (b) at least one of the enclosing wall or the door defining a venting pass through area; and
   (c) a filter occluding the venting passage area and forming a sealed interface with the at least one of the enclosing wall or the door, wherein a ratio of the venting pass through area to the interior volume is at least 4 square inches to 250 cubic inches.

2. The sterilization container of claim 1, wherein the ratio of the venting pass through area to the interior volume is between 4 square inches to 250 cubic inches and 6 square inches to 1 cubic inch.

3. The sterilization container of claim 1, wherein the venting pass through area is defined by at least one vent.

4. The sterilization container of claim 1, wherein the venting pass through area is defined by at least one vent port.

5. The sterilization container of claim 1, wherein the enclosing wall includes a sidewall, a top wall and a bottom wall and the venting pass through area is located in at least one of the sidewall, the top wall and the bottom wall.

6. The sterilization container of claim 1, wherein the door is moveable between an open and a closed position, and wherein the venting pass through area is in the door.

7. The sterilization container of claim 6, further comprising an opening in the enclosing wall, the opening lying in a plane spaced from a rear wall of the enclosing wall, wherein the door is moveable between an open position permitting passage of the tray through the opening into the interior volume and a closed position precluding passage of the tray through the opening.

8. The sterilization container of claim 1, wherein the venting pass through area is defined by a fenestration in the enclosing wall, and the enclosing wall includes a plurality of walls.

9. The sterilizing container of claim 1, wherein each of the enclosing walls and the door has a surface area, and wherein substantially all of the surface area of at least one of the enclosing walls and door is the venting pass through area.

10. The sterilizing container of claim 1, wherein the top wall, bottom wall, rear wall, right sidewall, left sidewall, and door have a total surface area, and wherein at least 8% of the total surface area of the sterilizing container comprises the venting pass through area.

11. The sterilizing container of claim 1, wherein the top wall, bottom wall, rear wall, right sidewall, left sidewall, and door have a total surface area, and wherein at least 15% of the total surface area of the sterilizing container comprises the venting pass through area.

12. A method of drying contents in a sterilization container, the method comprising:
   (a) placing contents in a sterilization container having a top wall, a bottom wall, a rear wall, a right sidewall, a left sidewall, and a door defining an interior volume sized to receive a plurality of instrument trays, each instrument tray sized to retain a plurality of medical instruments, wherein each of the top wall, bottom wall, rear wall, right sidewall and left sidewall is an enclosing wall, and wherein an opening extends between the left sidewall and the right sidewall and between the top wall and the bottom wall and lying in a plane spaced from the rear wall, and wherein the opening is sized to receive the plurality of instrument trays;

(b) having an enclosing wall and at least one door defining an interior volume sized to receive at least one instrument tray retaining the contents;

(c) moving the door from an open position to a closed position to seal the sterilization container;

(d) venting the sterilization container through a venting pass through area having a filter occluding the venting passage area, wherein a ratio of the venting pass through area to the interior volume is at least 4 square inches to 250 cubic inches; and (e) obtaining a drying of the contents in the sterilization container in less than 30 minutes.

13. The method of claim 12, wherein the ratio of the venting pass through area to the interior volume is between 4 square inches to 250 cubic inches and 6 square inches to 1 cubic inch.

14. The method of claim 12, wherein the drying is less than 15 minutes.

15. A sterilization container for retaining surgical instruments in a sterilizer, the sterilization container comprising:

(a) a top wall, a bottom wall, a rear wall, a right sidewall and a left sidewall of the sterilization container and a door defining an interior volume sized to receive a plurality of instrument trays, each instrument tray sized to retain a plurality of medical instruments, wherein each of the top wall, bottom wall, rear wall, right sidewall and left sidewall is an enclosing wall, and wherein an opening extends between the left sidewall and the right sidewall and between the top wall and the bottom wall and lying in a plane spaced from the rear wall, and wherein the opening is sized to pass the plurality of instrument trays;

(b) at least one of the enclosing wall and the door defining a venting pass through area; and (c) a filter occluding the venting pass through area and forming a sealed interface with the at least one of the enclosing wall and the door, the sterilization container having a ratio of the venting pass through area to the interior volume that is at least 4 square inches to 250 cubic inches and sufficient to provide a drying time of less than 30 minutes.

16. The sterilization container of claim 15, wherein the drying time is approximately 15 minutes for 140 lbs or less of instruments.

17. The sterilization container of claim 15, wherein the ratio of the venting pass through area to the interior volume is at least 4 square inches to 250 cubic inches.

18. The sterilization container of claim 15, wherein the ratio of the venting pass through area to the interior volume is between 4 square inches to 250 cubic inches and 1 square inch to 50 cubic inches.

19. The sterilization container of claim 15, wherein the ratio of the venting pass through area to the interior volume is between 1 square inch to 50 cubic inches and 1 square inch to 5 cubic inches.

* * * * *